United States Patent
Nikitin et al.

(10) Patent No.: US 9,659,216 B2
(45) Date of Patent: May 23, 2017

(54) METHOD, COMPUTER PROGRAM, AND SYSTEM FOR AUTOMATED REAL-TIME SIGNAL ANALYSIS FOR DETECTION, QUANITIFICATION, AND PREDICTION OF SIGNAL CHANGES

(75) Inventors: Alexei V. Nikitin, Lawrence, KS (US); Mark G. Frei, Oviedo, FL (US); Naresh C. Bhavaraju, Lawrence, KS (US); Ivan Osorio, Leawood, KS (US); Ruslan L. Davidchack, Wigston (GB)

(73) Assignee: Flint Hills Scientific, L.L.C., Lawrence, KS (US)

( * ) Notice: Subject to any disclaimer, the term of this patent is extended or adjusted under 35 U.S.C. 154(b) by 0 days.

(21) Appl. No.: 13/608,551

(22) Filed: Sep. 10, 2012

(65) Prior Publication Data

US 2013/0012825 A1    Jan. 10, 2013

Related U.S. Application Data

(63) Continuation of application No. 11/724,738, filed on Mar. 16, 2007, now Pat. No. 8,265,742, which is a (Continued)

(51) Int. Cl.
*G01N 33/48* (2006.01)
*G01N 33/50* (2006.01)
(Continued)

(52) U.S. Cl.
CPC ......... *G06K 9/00536* (2013.01); *G06F 17/10* (2013.01); *G06F 17/18* (2013.01);
(Continued)

(58) Field of Classification Search
None
See application file for complete search history.

(56) References Cited

U.S. PATENT DOCUMENTS

| | | |
|---|---|---|
| 4,663,703 A | 5/1987 | Axelby et al. |
| 4,791,548 A | 12/1988 | Yoshikawa et al. |
| | (Continued) | |

OTHER PUBLICATIONS

Osorio et al. Real-time automated detection and quantitative analysis of seizures and short-term prediction of clinical onset. Epilepsia, vol. 39, 1998, pp. 615-627.*
(Continued)

*Primary Examiner* — Russell S Negin
(74) *Attorney, Agent, or Firm* — CF3; Stephen Eisenmann

(57) ABSTRACT

A method, computer program, and system for real-time signal analysis providing characterization of temporally-evolving densities and distributions of signal features of arbitrary-type signals in a moving time window by tracking output of order statistic filters (also known as percentile, quantile, or rank-order filters). Given a raw input signal of arbitrary type, origin, or scale, the present invention enables automated quantification and detection of changes in the distribution of any set of quantifiable features of that signal as they occur in time. Furthermore, the present invention's ability to rapidly and accurately detect changes in certain features of an input signal can also enable prediction in cases where the detected changes associated with an increased likelihood of future signal changes.

6 Claims, 11 Drawing Sheets

Related U.S. Application Data continuation of application No. 10/911,031, filed on Aug. 4, 2004, now Pat. No. 7,188,053, which is a continuation of application No. 10/404,850, filed on Apr. 1, 2003, now Pat. No. 6,904,390, which is a continuation of application No. 09/824,946, filed on Apr. 3, 2001, now Pat. No. 6,768,969.

(60) Provisional application No. 60/194,130, filed on Apr. 3, 2000, provisional application No. 60/223,206, filed on Aug. 4, 2000.

(51) Int. Cl.
  *G06K 9/00* (2006.01)
  *G06F 17/10* (2006.01)
  *G06F 17/18* (2006.01)
  *G06F 19/24* (2011.01)
  *G06F 19/00* (2011.01)

(52) U.S. Cl.
  CPC ............ *G06F 19/24* (2013.01); *G06F 19/345* (2013.01); *G06F 19/3437* (2013.01)

(56) References Cited

U.S. PATENT DOCUMENTS

| | | | |
|---|---|---|---|
| 4,868,773 A | 9/1989 | Coyle et al. | |
| 4,998,051 A | 3/1991 | Ito | |
| 5,347,446 A | 9/1994 | Iino et al. | |
| 5,519,605 A | 5/1996 | Cawlfield | |
| 5,583,963 A | 12/1996 | Lozach | |
| 5,995,868 A | 11/1999 | Dorfmeister et al. | |
| 6,081,144 A | 6/2000 | Usuki et al. | |
| 6,121,817 A | 9/2000 | Yang et al. | |
| 6,768,969 B1 * | 7/2004 | Nikitin et al. | 702/188 |
| 8,265,742 B2 * | 9/2012 | Nikitin et al. | 600/544 |
| 8,562,536 B2 * | 10/2013 | Osorio et al. | 600/483 |

OTHER PUBLICATIONS

Edwards et al. Elementary Differential Equations with Boundary Value Problems, Third Edition. Prentice-Hall: Englewood Cliffs, New Jersey, 1993, Section 6.1, pp. 460-468.*

Sorting Continuous-Time Signals and the Analog Median Filter, Paulo J. S. G. Ferreira, IEEE Signal Processing Letters, vol. 7, No. 10, Oct. 2000, pp. 281-283.

A Review of Median Filter Systems for Analog Signal Processing, Tina Jarske and Olli Vainio, Analog Integrated Circuits and Signal Processing 3, pp. 127-135.

Median Filtering by Threshold Decomposition, J. Patrick Fitch, Edward J. Coyle, and Neal C. Gallagher, Jr., IEEE Transactions on Acoustics, Speech, and Signal Processing, vol. ASSP-32, No. 6, Dec. 1984, pp. 1183-1188.

Design and Implementation of a Single-Chip 1-D Median Filter, Kernal Oflazer, IEEE Transactions on Acoustics, Spech and Signal Processing, vol. ASSP-31, No. 5, Oct. 1983, pp. 1164-1168.

Direct Analog Rank Filtering, Kiichi Urahama and Takeshi Nagao, IEEE Transactions on Circuits and Systems-I:Fundamental Theory and Applications, vol. 42, No. 7, Jul. 1995, pp. 385-388.

Design of a Switched-Current Median Filter, C. K. Tse and K. C. Chun, IEEE Transactions on Circuits and Systems-II: Analog and Digital Signal Processing, vol. 42, No. 5, May 1995, pp. 356-359.

OSNet: A Neural Network Implementation of Order Statistic Filters, Pingnan Shi and Rabab K. Ward, IEEE Transactions on Neural Networks, vol. 4, No. 2, Mar. 1993, pp. 234-241.

Abstract of Analog Implementation of Seizure Detection Algorithm, Nikitin et. al., BMES/EMBS Conference, 1999. Proceedings of the First Joint, Oct. 13-16, 1999, pp. 860 vol. 2.

High Speed FPGA Implementation of Median Filters, Bela Feher and Gabor Szedo, NDES '98 Nonlinear Dynamics of Electronic Systems, Tech. University of Budapest, Hungary Jul. 16-18, 1998, p. 191-19.

Deterministic Properties of Analog Median Filters, Murk J. Borrema, IEEE Transactions on Information Theory, vol. 37, No. 6, Nov. 1991, pp. 1629-1640.

Analysis of the Properties of Median and Weighted Median Filters Using Threshold Logic and Stack Filter Representation, Olli Yii-Harja, Jaakko Astola and Yijo Neuvo, IEEE Transactions on Signal Processing, vol. 39, No. 2, Feb. 1991, pp. 395-410.

Properties of Analog Median Filters, Steffen Paul, Knut Huper adn Josef A. Nossek, Non-Linear Digital Signal Processing 1993, IEEE Writer Workshop Jan. 17-20, 1993.

Stack Filters, Peter D. Wendt, Edward J. Coyle, adn Neal C. Gallagher, IEEE Transactions on Acoustics, Speech and Signal Processing, vol. ASSP-34, No. 4, Aug. 1986, pp. 898-911.

Output Distributions of Recursive Stack Filters, Ilya Shmulevich, Olli Yii-Harja, Karen Egiazarian, and Jaakko Astola, IEEE Signal Processing Letters, vol. 6, No. 7, Jul. 1999, pp. 175-178.

Binary Partition Algorithms and VLSI Architectures for Median and Rank Order Filtering, Charng Long Lee and Chein-Wei Jen, IEEE Transactions on Signal Processing, vol. 41, No. 9, Sep. 1993, pp. 2937-2942.

A New Algorithm for Order Statistic and Sorting, Barun K. Kar and Dhiraj K. Pradhan, IEEE Transactions on Signal Processing, vol. 41, No. 8, Aug. 1993, pp. 2688-2694.

Frei, Mark G., Parametric Identification in Continuous-Time Stochastic Systems Using Time and Space Weighted Least Squares, Dissertation, Dec. 7, 1993, submitted to the University of Kansas Department of Mathematics.

Nikitin, Alexei V., Pulse Pileup Effects in Counting Detectors, Dissertation, submitted to the University of Kansas Department of Physics and Astronomy, published Aug. 29, 1999.

Nikitin, Alexei V. et al., Many-fold Coincidence Pileup in Silicon Detectors: Solar X-Ray Response of Charged Particle Detector Systems for Space, Elsevier Science, Aug. 16, 1996.

Nikitin, Alexei V., et al., The effect of pulse pile-up on threshold crossing rates in a system with a known impulse response, Elsevier Science, Nov. 15, 1997.

* cited by examiner

METHOD, COMPUTER PROGRAM, AND SYSTEM FOR AUTOMATED REAL-TIME SIGNAL ANALYSIS FOR DETECTION, QUANITIFICATION, AND PREDICTION OF SIGNAL CHANGES

CROSS-REFERENCE TO RELATED APPLICATIONS

The present application is a continuation application of Ser. No. 11/724,738, which is a continuation application of Ser. No. 10/911,031, which is a continuation application of Ser. No. 10/404,850, which is a continuation application of Ser. No. 09/824,946, which is hereby incorporated into the present application by reference. The present application relates to and claims priority with regard to all common subject matter of a first provisional patent application titled "Methods for Signal Analysis, Order Statistic Signal Normalization, and Analog Implementation of Order Statistic Filters", Ser. No. 60/194,130, filed Apr. 3, 2000. The identified first provisional patent application is hereby incorporated into the present application by reference.

The U.S. Government has a paid-up license in this invention and the right in limited circumstances to require the patent owner to license others on reasonable terms as provided for by the terms of Grant No. 5R44NS34630-03 awarded by the National Institutes of Health/National Institute of Neurological Disorders and Stroke (NINDS).

COMPUTER PROGRAM LISTING APPENDIX

A computer program listing appendix containing the source code of a computer program that may be used with the present invention is incorporated herein by reference and appended to application Ser. No. 09/824,946 as one (1) original compact disk, and an identical copy thereof, containing a total of forty-one (41) files as follows:

| Filename | Date of Creation | Size (Bytes) |
|---|---|---|
| AMPLDIST.M | 03/12/1999 12:23p | 2,736 |
| APTF.C | 08/06/1999 12:33p | 8,146 |
| DIGITI~1.C | 06/26/1999 02:38p | 5,520 |
| DIGITI~1.M | 06/26/1999 02:39p | 627 |
| DISTR1D.M | 06/17/1999 12:45p | 3,984 |
| DISTR2D.M | 06/26/1999 02:40p | 5,702 |
| DISTRI~1.C | 10/13/1999 02:24p | 8,218 |
| EST_ER~1.M | 03/27/2001 04:34p | 330 |
| FGTOBG~1.C | 10/22/1999 09:45a | 9,730 |
| FGTOBG~2.C | 10/22/1999 10:15a | 9,917 |
| KSEEG2.C | 10/22/1999 11:59a | 6,606 |
| KSSAPP~1.C | 10/19/1999 03:32p | 11,997 |
| LOCATE.M | 07/16/1999 10:02a | 542 |
| PTCFIL~1.C | 08/04/1999 08:42a | 8,707 |
| PTCFIL~1.M | 07/24/1999 10:42a | 935 |
| PTF.C | 10/06/1999 12:22p | 7,337 |
| PTF1.M | 09/07/2000 01:32p | 847 |
| PTF2.M | 09/07/2000 01:33p | 734 |
| PTFHIL~1.C | 10/06/1999 04:08p | 7,361 |
| PTFILTER.C | 08/04/1999 08:43a | 7,481 |
| PTFILTER.M | 07/24/1999 10:48a | 801 |
| PTFSQR.C | 10/15/1999 11:56a | 6,901 |
| PTF_CHI.CPP | 02/14/2001 05:58p | 3,829 |
| PTF_CHI.M | 02/13/2001 06:02p | 477 |
| PTF_DEMO.M | 04/02/2001 12:32a | 1,101 |
| PTF_NOR.CPP | 02/16/2001 05:26p | 3,618 |
| PTF_NOR.M | 11/20/2000 01:28p | 532 |
| PTF_TRI.CPP | 03/05/2001 01:12p | 3,387 |
| PTF_TRI.M | 02/16/2001 05:33p | 548 |
| PTF_UNI.CPP | 02/20/2001 06:47p | 3,110 |
| PTF_UNI.M | 10/30/2000 11:25a | 451 |

-continued

| Filename | Date of Creation | Size (Bytes) |
|---|---|---|
| QKS.C | 10/11/1999 02:16p | 3,959 |
| REXPMEAN.C | 08/09/1999 11:40a | 3,544 |
| RMEAN.C | 09/13/1999 01:48p | 3,532 |
| RMEAN.M | 07/27/1999 03:35p | 588 |
| RMEANM~1.C | 09/13/1999 09:10p | 5,464 |
| THRESH~1.C | 07/06/1999 11:11a | 8,932 |
| THRESH~1.M | 03/03/1999 04:50p | 1,028 |
| THRESH~2.M | 03/04/1999 12:00p | 3,218 |
| THRESH~3.M | 06/16/1999 06:03p | 1,386 |
| UNI_2_~1.M | 03/05/2001 01:27p | 417 |

BACKGROUND OF THE INVENTION

1. Field of the Invention

The present invention relates generally to methods, computer programs and systems for automated signal analysis providing rapid and accurate detection, prediction, or quantification of changes in one or more signal features, characteristics, or properties as they occur. More particularly, the present invention relates to a method, computer program, or system for automated real-time signal analysis providing characterization of temporally-evolving densities and distributions of signal features of arbitrary-type signals in a moving time window by tracking output of order statistic filters (also known as percentile, quantile, or rank-order filters).

2. Description of the Prior Art

It is often desirable to detect and quantify feature changes in an evolving signal, and there have been numerous attempts to develop automated signal analysis means operable to do so. One well-known approach, for example, is based upon analysis of the signal's mean value, which is typically a well known, well understood, and easily computed property. Other well-known techniques look for changes in signal variance or standard deviation over time. Unfortunately, these commonly used approaches have significant drawbacks, including lack of robustness in the presence of signal outliers. Furthermore, in all but a few ideal cases, monitoring these individual parameters does not enable detection of all types of changes in feature distribution. This is because the mean and standard deviation rarely completely describe the signal distribution. Another problem that plagues many existing analysis techniques is that they are unable to deal adequately with real-world problems in which the analyzed signal is often highly complex, non-stationary, non-linear, and/or stochastic.

Another well-known approach, one more suited to practical situations than the above-mentioned methods, uses order statistics (e.g., the median or other percentile or quantile values). Order statistics are advantageous because they are directly related to the underlying distribution and are robust in the presence of outliers. For example, a method of signal analysis that enables the detection of state changes in the brain through automated analysis of recorded signal changes is disclosed in U.S. Pat. No. 5,995,868. This method addresses the problem of robustness in the presence of outliers through novel use of order-statistic filtering. Additionally, given information from a moving time window of a certain time scale, referred to as the "foreground", this method provides for real-time comparison thereof with a reference obtained from past data derived, e.g., from a longer time scale window, referred to as the "background." This approach thereby addresses some of the normalization problems associated with complex, non-stationary signals.

Although the prior invention disclosed in U.S. Pat. No. 5,995,868 has successfully addressed many of the above-mentioned limitations, including normalization problems associated with complex non-stationary signals, it is lacking in breadth of scope. Detection of changes, for example, is limited to a particular order statistic of the signal. Additionally, the order statistic filter employed to detect signal changes requires large amounts of processing ability, memory, and power when used on digital signals for which sorting procedures are performed at each point in time. Furthermore, the method does not enable full analog implementation.

Most work on order statistic filters, such as median filters, and their implementation is in the areas of digital signal and image processing, which, as mentioned, requires large amounts of processing ability, memory, and power not practical or cost-effective for some applications. Work on analog median filters is limited to situations where the input is provided as parallel lines of data, and a program or circuit that implements the filter outputs a value that is equal to the median of the data on different input lines. Work on analog median filtering for continuous-time signals is not extensive, and no realizable implementations exist able to track a percentile (e.g., median) of a continuous-time signal. One reason for this is that the operation of finding the rank or order is non-linear, making modeling the procedure using an ordinary differential equation so complicated that it has not yet been addressed.

Due to the above-described and other problems, a need exists for a more general, powerful, and broad method for automated analysis of signals of any degree of complexity and type.

SUMMARY OF THE INVENTION

The present invention solves the above-described and other problems to provide a distinct advance in the art of automated signal analysis. More specifically, the present invention comprises a method, computer program, and system for real-time signal analysis providing characterization of temporally-evolving densities and distributions of signal features of arbitrary-type signals in a moving time window by tracking output of order statistic filters (also called percentile, quantile, or rank-order filters).

The present invention is operable to analyze input signals of arbitrary type, origin and scale, including, for example, continuous-time or discrete-time, analog or digital, scalar or multi-dimensional, deterministic or stochastic (i.e., containing a random component), stationary (i.e., time invariant) or non-stationary (i.e., time varying), linear or nonlinear. Thus, the present invention has broad applicability to analysis of many different types of complex signals and sequences of data, including but not limited to biological signals such as those produced by brain, heart, or muscle activity; physical signals such as seismic, oceanographic, or meteorological; financial signals such as prices of various financial instruments; communication signals such as recorded speech or video or network traffic signals; mechanical signals such as jet engine vibration; target tracking and recognition; signals describing population dynamics, ecosystems or bio-systems; signals derived from manufacturing or other queuing systems; chemical signals such as spectroscopic signals; and sequences of data such as word lists, documents, or gene sequences. Furthermore, the present invention is applicable to any set of signal features so long as they are quantifiable, thereby allowing for a high degree of system adaptability and selectivity.

Thus, the present invention enables automated detection and quantification of changes in the distribution of any set of quantifiable features of a raw input signal as they occur in time. The input signal, denoted as $\{x(t)\}$, can be any data parameterized by a real-valued variable, t, which will be interpreted as a time variable. The input signal may be optionally preprocessed in order to produce a new signal, the feature signal, denoted as $\{X(t)\}$ $\{X(t)\}$ quantifies a set of features of the input signal that the system will use in detecting and quantifying changes. For a fixed t, X(t) is called the signal feature vector at time t. The feature vector has as many components as there are signal features. While potentially of substantial value, this preprocessing step is optional in the sense that the raw input signal itself may be used as the feature vector (i.e., $X(t)=x(t)$), in which case the invention proceeds to detect changes in the distribution of the raw input signal as it evolves in time. The desirability of preprocessing will depend upon the nature of the raw input signal and the nature of the features of interest.

The present invention also introduces a useful new object called the time-weighted feature density of a signal, $\{f(t,X)\}$, which can be computed from the feature signal at each point in time. This object allows access to estimates of the full time-dependent density and cumulative distribution function of varying signal features with any desired degree of accuracy, but confines these estimates to any desired time-scale through the use of time-weighting (time localization of feature density). This time-weighted feature density describes the raw input signal features measured in moving windows of time specified by the time-weight function, which allows a user to apply different significances to portions of available information (e.g., to consider recent information as more relevant than older information; or to weight information according to its reliability, etc.).

Moreover, the present invention allows for rapidly obtaining these estimates in a computationally efficient manner that can be implemented in digital or analog form, and a method for detecting, quantifying, and comparing changes of arbitrary type in the density/distribution of the feature vector as it changes. The significance of this increase in computational efficiency, along with analog implementability, becomes especially clear when considering medical device applications where, for example, the present invention enables currently used externally-worn devices that require daily battery recharging to become fully implantable devices with an operational lifetime of several years, thereby improving safety and convenience.

In operation, a raw time-varying input signal of arbitrary type, origin, and scale is received for analysis. Optionally, depending upon the nature of the raw input signal and the nature of the features of interest, pre-processing occurs to produce a feature signal more amenable to further analysis. Next, time-weighted density or distribution functions are determined for both a foreground or current time window portion of the signal and a background portion of the signal or reference signal (which also may be evolving with time, but potentially on a different timescale) in order to emphasize, as desired, certain data.

Percentile values for both foreground and background signals are then accurately estimated and compared so as to detect and quantify feature changes on any timescale and to any desired degree of precision as the raw input signal evolves in time. Density and distribution approximations may also be compared. As noted above, the state of the existing art requires that the data be laboriously sorted in order to determine these percentile values. In the present invention, however, percentile values are accurately estimated without sorting or stacking, thereby increasing processing speed and efficiency while reducing computation, memory, and power needs. Thus, the present invention is able to perform in a highly computationally efficient manner that can be implemented in a low power consumption apparatus consisting of an analog system, a digital processor, or a hybrid combination thereof, thereby providing tremendous system power savings.

The present invention is also operable to facilitate real-time signal normalization with respect to the density/distribution approximations, which is useful in processing and analysis of series of different orders. This is particularly useful where the features or characteristics of interest are invariant to a monotonic transformation of the signal's amplitude.

It will also be appreciated that the present invention's ability to rapidly and accurately detect changes in certain features of the input signal can enable prediction in cases where the changes it detects are associated with an increased likelihood of future signal changes. For example, when applied to seismic signals, the method can enable prediction of an earthquake or volcanic eruption; when applied to meteorological signals, the method can enable prediction of severe weather; when applied to financial data, the method can enable prediction of an impending price change in a stock; when applied to brain waves or heart signals, the method can enable prediction of an epileptic seizure or ventricular fibrillation; and when applied to brain wave or electromyographic signals, it can enable prediction of movement of a body part.

These and other novel features of the present invention are described in more detail herein below.

BRIEF DESCRIPTION OF THE DRAWING FIGURES

The present invention is described in detail below with reference to the attached drawing figures, wherein.

DETAILED DESCRIPTION OF A PREFERRED EMBODIMENT

The present invention comprises a method, computer program, and system for real-time signal analysis providing characterization of temporally-evolving densities and distributions of signal features of arbitrary-type signals in a moving time window by tracking output of order statistic (e.g., percentile, quantile, rank-order) filters. More specifically, given a raw input signal of arbitrary type, origin, and scale, the present invention enables automated quantification and detection of changes in the distribution of any set of quantifiable features of that signal as they occur in time. Furthermore, the present invention's ability to rapidly and accurately detect changes in certain features of an input signal can also enable prediction in cases when the detected changes are associated with an increased likelihood of future signal changes.

METHOD

Step 1: Receive Raw Input Signal

Figure 1:
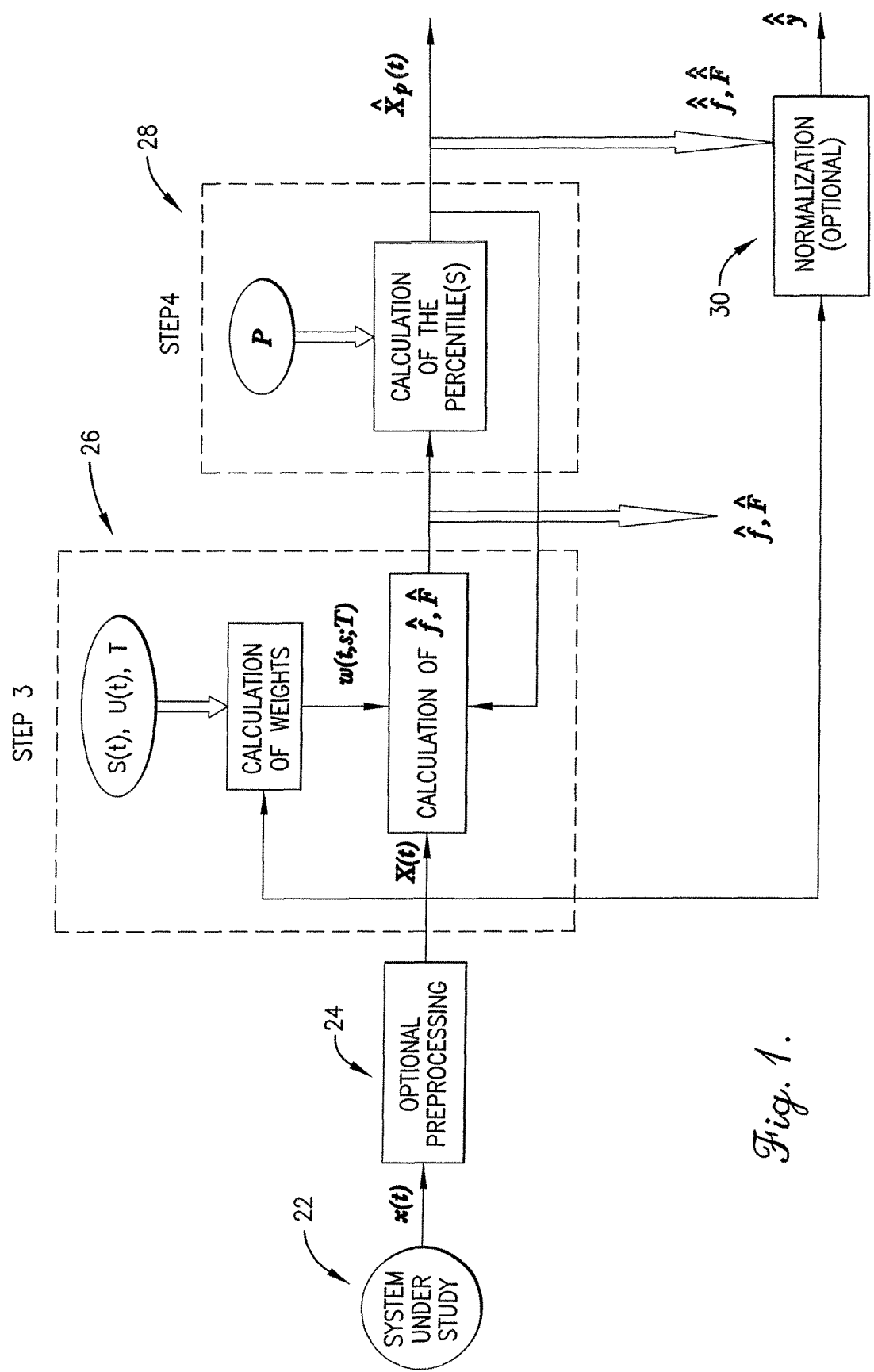
FIG. 1 is a block diagram illustrating a first portion of steps involved in performing a preferred embodiment of the present invention.

Referring to FIG. 1, the raw input signal is received from a system under study 22. This signal, denoted as $\{x(t)\}$, can be any data parameterized by a real-valued variable, t, which will be interpreted as a time variable. As noted, the raw input signals may be of arbitrary type, including, for example, continuous-time or discrete-time, analog or digital, scalar or multi-dimensional, deterministic or stochastic (i.e., containing a random component), stationary (i.e., time invariant) or non-stationary (i.e., time varying), and linear or nonlinear. The raw input signals may also be of arbitrary origin, including, for example, biological signals such as those produced by brain, heart, or muscle activity; financial signals such as prices of various financial instruments; physical signals such as seismic, oceanographic, and meteorological; communication signals such as recorded speech or video or network traffic signals; mechanical signals such as jet engine vibration; chemical signals such as those obtained in spectroscopy; and sequences of data such as word lists or gene sequences.

Step 2: (Optional) Preprocess Raw Input Signal to Derive Feature Signal

The raw input signal may be optionally pre-processed, as shown in box 24, in order to produce a new signal, the feature signal, denoted as $\{X(t)\}$. One skilled in the art will appreciate that there exist a nearly endless set of transformations that can be applied to the raw input signal, x(t), to quantify various features, characteristics, or properties of the signal as it evolves. Common examples include derivatives of any order; integrals or any order; various moments and related properties such as variance, skewness, kurtosis; wavespeed and related measures such as inter-zero-crossing intervals and inter-peak intervals; signal power in a time window and/or in a particular frequency band; measures derived from Fourier analysis such as those involving signal phase or power spectral density; measures from nonlinear dynamics such as correlation dimension, fractal dimension, magnitude of Lyapunov exponents; phase delay embeddings; and measures of rhythmicity, wave shape, or amplitude.

The feature signal, $\{X(t)\}$, quantifies a set of features of the input signal that the system will use in detecting changes. For a fixed t, X(t) is called the signal feature vector at time t. The feature vector has as many components as there are signal features. While potentially of substantial value, this pre-processing step is optional in the sense that the raw input signal itself may be used as the feature vector (i.e., X(t)=x(t)), in which case the invention proceeds to detect changes in the distribution of the raw signal as it evolves in time. The desirability of preprocessing will depend upon the nature of the raw input signal and the nature of the features of interest.

Step 3: Determine Time-Weighted Distribution and Density Functions of the Feature Signal A time-weighted feature density (TWFD) of a signal, $\{f(t,X)\}$, is computed from the raw input signal or feature signal at each point in time, as shown in box 26. The TWFD allows access to estimates of the full time-dependent density and cumulative distribution functions of varying signal features with any desired degree of accuracy, but confines these estimates to any desired time-scale through the use of time-weighting (time localization of feature density). Time-weighting allows the user to apply different significance to portions of available information (e.g., to consider more recent information as more relevant than older information; or to weigh information according to its reliability, etc.).

Thus, the TWFD describes the raw input signal features measured in moving windows of time specified by a time-weight function, thereby allowing for detection, quantification, and comparison of changes of arbitrary type in the density/distribution of the feature vector as it evolves.

The instantaneous feature density of a signal, X, at time t is defined as $$f(t,D) = \delta[D - X(t)], \quad (1)$$

where $\delta(x)$ is the Dirac $\delta$-function, and D is a variable signal level. This density is just a $\delta$-function at the signal's present value.

The concept of instantaneous feature density can then be extended to a time-weighted window. The TWFD of the feature signal X(t) in a time window w(t,s) is defined as $$f(t, D) = \int_{-\infty}^{\infty} w(t, s)\delta[D - X(s)]ds, \quad (2)$$

where $\delta(x)$ is the Dirac $\delta$-function, D is the amplitude, and the weighting function, w(t,s), often called a "time-weight," is any function such that $$\int_{-\infty}^{\infty} w(t, s)ds = 1. \quad (3)$$

Typically, $w(t,s) \geq 0$ for all t,s. Also, in most practical applications, w will be "causal" meaning that w(t,s)=0 for all s>t. It should be noted that w(t,s) may attain its dependence upon t or s through an explicit dependence upon other signals (e.g., X(t), in which case it may be referred to as a "state-weight").

When w(t,s)=w(t−s), Eq. (2) becomes a convolution integral, and the time-weighting function is interpreted as a moving window. If T is a characteristic time, or duration of w, the dependence may be expressed as w(t,s; T), and a shorthand notation used for the integral $$\int_{-\infty}^{\infty} w(t-s; T)...ds = \langle ... \rangle_T. \quad (4)$$

Eq. (4) defines a time average on a time scale T. In the notation, w(t,s; T), the independent variable, s, is used as the domain of the function, the independent variable, t, represents the current time, and is used to parameterize the choice of w, enabling the time window to change or move as time changes or evolves. This dependence on t also allows the user to change the shape of time-weighting as t changes. Moreover, the time scale can vary with time (i.e., T=T(t)). The weight function may also depend upon other information besides time (e.g., the raw signal, the feature signal, signals derived from the feature signal (such as it's time derivatives), other "auxiliary" signals, S(t), or control signals, U(t)). This generalization allows for state-weighting as mentioned above, or to, e.g., include other "outside" information into the analysis, emphasizing feature signal information accordingly.

$f(t,D)$ of Eq. (2) reduces to the instantaneous density defined by Eq. (1) when $w(t,s)=\delta(t-s)$. The notation of Eq. (4) may be used for both continuous and discrete time averages.

For example, the time window may be a rectangular moving window of length T, such that $$w(t, s; T) = w(t-s) = \frac{1}{T}\theta[(T - (t-s))(t-s)], \quad (5)$$

where $\theta(x)$ is the Heaviside step function, it results that $$f(t, D; w) = \langle \delta[D - X(s)] \rangle_T = \frac{1}{T} \int_{t-T}^{t} \delta[D - X(s)]ds. \quad (6)$$

In another example, the time window may be an exponential moving window with time constant T, such that $$w(t, s; T) = w(t-s) = \frac{1}{T}\exp\left(\frac{s-t}{T}\right)\theta(t-s), \quad (7)$$

wherein it results that $$f(t, D; w) = \langle \delta[D - X(s)]\rangle_T = \frac{1}{T}\int_{-\infty}^{t}\exp\left(\frac{s-t}{T}\right)\delta[D - X(s)]ds. \quad (8)$$

This particular choice of weight is the preferred embodiment for all analog implementations because of its ease of use.

A time-weighted cumulative distribution function (TW-CDF) of the feature signal, F(t,x;w), can now be derived. The TWCDF describes the distribution of the feature signal in a time window that is weighted according to the time-weight function, w (hence the notational dependence of F on w). This time-weight determines how information from the feature signal will contribute to the probability distribution, and is described in more detail below.

It will be appreciated that the TWFD can be obtained from the TWCDF by differentiation, and the TWCDF obtained from the TWFD via integration as follows:

$$f(t, x; w) = F_x(t, x; w), \quad (9)$$

$$F(t, x; w) = \int_{-\infty}^{x} f(t, y; w)dy. \quad (10)$$

It is easy to see from Eq. (10) and the well known identities relating the Dirac δ-function and Heaviside functions:

$$\theta(x) \equiv \int_{-\infty}^{x}\delta(s)ds, \quad (11)$$

and $$\delta(x) = \frac{d}{dx}\theta(x), \quad (12)$$

that all equations for feature densities (Eqs. (2), (6), and (8)) hold for cumulative distribution as well, provided that symbols "f" and "δ" in these equations are replaced by "F" and "θ", respectively.

As will be appreciated by one with ordinary skill in the art, percentile values are the very building blocks of probability distributions and enable a robust statistical description thereof. In many applications they produce significantly better information than other more commonly utilized statistics such as the mean and standard deviation. The set of all percentile values completely describes the distribution from which they are derived.

Given any number p∈[0,1], the $p^{th}$ percentile, $X_p(t)$, of the TWCDF, F(t,x; w) is defined implicitly by the equation $$F(t, X_p(t;w);w) = p. \quad (13)$$

Differentiating the above equation with respect to t, we see that $$F_t(t, X_p) + F_X(t, X_p)\dot{X}_p(t) = 0 \quad (14)$$

In the above equation, $F_t$ and $F_x$ denote the partial derivatives of F with respect to t and X, respectively. Rearranging terms results in $$\dot{X}_p(t) = -\frac{F_t(t, X_p)}{F_X(t, X_p)}. \quad (15)$$

The denominator of the above equation is the probability density function, $f(t,X; w)$, referred to as the "time-weighted feature density." Thus, $$\dot{X}_p(t) = -\frac{F_t(t, X_p)}{f(t, X_p)}; X_p(0) = X(0). \quad (16)$$

The solution to this important differential equation is the $p^{th}$ percentile, $X_p(t)$. In other words, $X_p(t)$ is the $p^{th}$ percentile of the time-varying cumulative distribution function, F(t,X;w), generated by the variations of the feature signal, X(t), in the temporal window defined by w.

In most practical applications, the TWCDF will not be known (or immediately available for on-line use) at each moment in time and will instead need to be approximated from available information.

One method of estimating the TWCDF (or the corresponding TWFD) is accomplished by partitioning the state space (containing the range of the feature signal) and computing time-weighted histograms that keep track of how often each bin is visited by the feature signal. This non-parametric approach to obtaining $\hat{F}(t,x;w)$ has the advantage (over the parametric approach described later herein) of allowing greater flexibility in approximating the TWCDF with any level of precision desired (although as precision improves, complexity of the implementation increases).

The feature density for discrete (digitally sampled) data can be computed in finite differences as follows (suppressing dependence on w):

$$\hat{f}(t, D_j) = \frac{1}{D_{j+1} - D_{j-1}}[\hat{F}(t, D_{j+1}) - \hat{F}(t, D_{j-1})] \quad (17)$$

$$= \frac{1}{D_{j+1} - D_{j-1}}\langle\theta\{[D_{j+1} - X(s)][D_{j-1} - X(s)]\}\rangle_T$$

or $$\hat{f}_{ij} = \hat{f}(t_i, D_j) = \sum_k w_{i-k}\theta_{ij} \quad (18)$$

where $$w_{i-k} = \frac{1}{2}(t_{i+1} - t_{i-1})w(t_i - t_k), \text{ and}$$

$$\theta_{ij} = \theta((D_{j+1} - X(t_i))(D_{j-1} - X(t_i))).$$

When the discrete character of the data is not intrinsic but a result of sampling and digitization of a continuous signal, then some kind of interpolation between the consecutive data points can often be appropriate. Then the identity $$\delta[a - f(x)] = \sum_i \frac{\delta(x - x_i)}{|f'(x_i)|} \quad (19)$$

can be utilized to compute the feature density. In Eq. (19), |f'(x)| denotes the absolute value of the function derivative with respect to x and the sum goes over all $x_i$ such that $f(x_i)=a$. For example, if linear interpolation is adequate, one can use $w_{i-k}=(t_{i+1}-t_i)w(t_i-t_k)$, and $$\theta_{ij} = \begin{cases} 1 & \text{if } D_j \le X(t_i) < D_{j+1}, D_j \le X(t_{i+1})D_{j+1} \\ \frac{D_{j+1} - D_j}{|X(t_{i+1}) - X(t_i)|} & \text{if } X(t_i) < D_j, X(t_{i+1}) \ge D_{j+1} \\ \frac{X(t_{i+1}) - D_j}{X(t_{i+1}) - X(t_i)} & \text{if } X(t_i) < D_j, D_j \le X(t_{i+1}) < D_{j+1} \\ \frac{D_{j+1} - X(t_i)}{X(t_{i+1}) - X(t_i)} & \text{if } D_j \le X(t_i) < D_{j+1}, X(t_{i+1}) \ge D_{j+1} \\ \frac{D_{j+1} - X(t_{i+1})}{X(t_i) - X(t_{i+1})} & \text{if } X(t_i) \ge D_{j+1}, D_j \le X(t_{i+1}) < D_{j+1} \\ \frac{X(t_i) - D_j}{X(t_i) - X(t_{i+1})} & \text{if } D_j \le X(t_i) < D_{j+1}, X(t_{i+1}) < D_j \end{cases} \quad (20)$$

In order to compute the approximation to the cumulative distribution, the following formula may be used:

$$\hat{F}(t, D) = \sum_{i=0}^{N-1} \left[ \hat{F}_i(t) + [\hat{F}_{i+1}(t) - \hat{F}(t)] \frac{D - D_i}{D_{i+1} - D_i} \right] \theta[(D - D_i)(D_{i+1} - D)], \quad (21)$$

where $\hat{F}_i(t) = <\theta[D_i - X(s)]>_T$, and $D_O$ and $D_N$ are such that $\hat{F}_O(t)=0$ and $\hat{F}_N(t)=1$, respectively (i.e., selected so that the signal never goes outside the interval $[D_0, D_N]$). It will be appreciated that the cumulative distribution function approximation obtained using by Eq. (21) is a continuous function of D. It will also be appreciated that, for a given s, $\theta[D_i-X(s)]$ need not be evaluated at each $D_i$. Instead, a binary search can be used to find i such that $D_i \le X(s) < D_{i+1}$.

Another method of estimating the TWCDF (or the corresponding TWFD) is accomplished by approximating F(t,x; w) by a model distribution function, $\tilde{F}(t,x;w,v(t))$, that may depend upon a vector of parameters, v(t). Some typical examples include a Gaussian (normal), or chi-squared distribution with $v(t)=[\mu(t)\sigma(t)]$, (the mean and standard deviation); a uniform distribution with $v(t)=[a(t)b(t)]$ (the left and right endpoints); a triangular distribution with $v(t)=[a(t) b(t) c(t)]$ (the left, vertex, and right endpoints of the density, respectively); or an exponential distribution with $v(t)=\lambda(t)$, the inverse of the distribution's mean.

An estimate, $\hat{v}(t)$, may then be obtained of the parameter vector, v(t), from information available up to time t. This facilitates a "parametric" estimate of $\hat{F}(t,x;w)=\tilde{F}(t,x;w,\hat{v}(t))$, by substituting the present parameter estimate into the model distribution.

The true feature density is typically unavailable for online analysis but may be well-approximated, assuming the distribution is well-modeled by a parametric distribution, through estimation of the parameters upon which the distribution depends. Often the moments of the distribution may be computed and used as input to the model to determine the approximation.

For example, a Gaussian approximation can be achieved using the first two moments (the mean, $\mu$, and the variance, $\sigma$) of the feature signal. More precisely, the model density $$\tilde{f}(t, x; T, [\mu \; \sigma]) = \frac{1}{\sqrt{2\pi\sigma}} \exp\left[-\frac{(x - \mu)^2}{2\sigma}\right] \quad (22)$$

is used, along with the parameter estimators $$\hat{v}(t) = [\hat{\mu}(t)\hat{\sigma}(t)] = [<X>_T <X>_T^2 - (<X>_T)^2], \quad (23)$$

to obtain $$\hat{f}(t,x;T) = \tilde{f}(t,x;T,\hat{v}(t)). \quad (24)$$

Similarly other parametric approximations for data may be used, such as uniform or triangular distributions. Though the true distribution of the data is not exactly known, approximations work well because the algorithm tracks the percentile at each instant in real time. The uniform and triangular distributions have the advantage of stability, faster processing, and, most importantly, ease of hardware implementation over others that involve exponentiation. The presence of the exponential function for Gaussian and Chi-squared distributions (for absolutely positive data) increases computation in software and complexity of hardware, but may also be used. The uniform distribution model reduces the complexity of implementing circuitry by an order of magnitude. This reduction is significant in reducing the size and power requirement of the circuit and significantly improves scope for miniaturization and possible embedded applications. Further, the uniform distribution makes the implementation stable, unlike the Gaussian approximation which requires signal limiting (clipping) to prevent output from becoming unbounded due to the exponential function. Similarly, the use of a triangular distribution model for data that is strictly positive simplifies the implementation (assuming the left end and vertex of the density are at x=0, the distribution is completely specified by the right endpoint, i.e., the maximal x value). The triangular distribution approximation can also be used to estimate the distribution of the signal from a single percentile calculation. One with ordinary skilled in the art will appreciate that similar parametric modeling and estimation may be performed using any other distribution model and parameter estimation scheme meant to approximate the underlying true density/distribution.

Step 4: Compute the Percentile Tracking Filter (PTF)

Once the TWCDF estimate, $\hat{F}(t,x;w)$, has been obtained (and the TWFD estimate, $\hat{f}(t,x;w)$, is therefore also available), an estimator of $X_p(t)$, referable to as the output of a percentile tracking filter (PTF) at time t, and denoted by $\hat{X}_p(t)$, is obtained, as shown in box 28, from the differential equation $$\dot{\hat{X}}_p(t) = -\frac{\hat{F}_t(t, \hat{X}_p)}{\hat{f}(t, \hat{X}_p)}; \; \hat{X}_p(0) = X(0). \quad (25)$$

One with ordinary skill in the art will appreciate that p may denote a vector of percentile values, (i.e., $p=[p_1 \; p_2 \; \ldots \; p_n]$) in which case $\hat{X}_p(t)$ denotes the vector $[\hat{X}_{p_1}(t) \; \hat{X}_{p_2}(t) \; \ldots \; \hat{X}_{p_n}(t)]$.

In certain applications, it is desirable to know the value of $X_p(t)$ such that $F(t,X_p;w)=p=$constant. Thus, $X_p(t)$ is an output of a rank-order (also order statistic, quantile, or percentile) filter. For example, $X_{1/2}(t)$ is the output of a median filter, producing at each moment in time the median of the w-weighted distribution of feature signal information in the most recent window.

Numerical rank-order filtering is a computationally expensive operation. First, it requires knowing, at any given time, the values of N latest data points, where N is the length of the moving window, and the numerical and chronological order of these data points. This memory requirement is a major obstacle to implementing an analog order statistic filter. Another computational burden on different (numerical) rank-order filtering algorithms results from the necessity to update the numerically ordered/sorted list, i.e., to conduct a search. Overall performance of a rank-order filter is a trade-off between performance, speed, and memory requirements.

$\hat{X}_p(t)$ is the $p^{th}$ percentile of $\hat{F}(t,x;w)$ in a moving window $w(t,s;T)=w(t-s;T)$ if $$\hat{F}(t, \hat{X}_p; T) = \qquad (26)$$
$$\int_{-\infty}^{\hat{X}_p} \hat{f}(t, D; w) dD = \int_{-\infty}^{\infty} w(t-s; T)\theta[\hat{X}_p(t) - X(s)] ds = p,$$

where $0 \leq p \leq 1$ is the percentile value. The time derivative of $\hat{X}_p$ can now be computed as $$\dot{\hat{X}}_p(t) = \qquad (27)$$
$$-\frac{\hat{F}_t(t, \hat{X}_p; w)}{\hat{f}(t, \hat{X}_p; w)} = -\frac{1}{\hat{f}(t, \hat{X}_p; w)} \int_{-\infty}^{\infty} \dot{w}(t-s; T)\theta[\hat{X}_p - X(s)] ds.$$

Typically $w(\bullet)$ is chosen such that it vanishes at $\pm\infty$, and since $$\dot{w}(t-s) = -\frac{d}{ds}w(t-s),$$

integration of Eq. (27) by parts leads to $$\dot{\hat{X}}_p(t) = \frac{1}{\hat{f}(t, \hat{X}_p; w)} \int_{-\infty}^{\infty} w(t-s; T)\{\dot{X}(s)\delta[\hat{X}_p(s) - X(s)]\} ds. \qquad (28)$$

$$= \frac{1}{\hat{f}(t, \hat{X}_p; w)} \sum_i w(t-t_i)\text{sign}[\dot{X}(t_i)], \qquad (29)$$

where the sum goes over all $t_i$ such that $X(t_i)=X_p(t)$, i.e., over all times of threshold crossings, using the identity of Eq. (19).

It will be appreciated that if $w(\bullet)$ has a shape that coincides with the impulse response of an analog filter, then the differential equation Eq. (27) can be solved in an analog circuit, provided that $\hat{f}(t,x;w)$ is evaluated in finite differences according to Eq. (17).

For example, where the time-weight function is a rectangular moving window of length T, $$\dot{\hat{X}}_p = \frac{1}{T\hat{f}(t, \hat{X}_p; T)}\{\theta[\hat{X}_p - X(t-T)] - \theta[\hat{X}_p - X(t)]\}. \qquad (30)$$

The braced expression is merely the total number of upward crossings of the threshold, $\hat{X}_p(t)$, by the signal minus the total number of downward crossings, in agreement with Eq. (29).

In another example, where the time-weight function is an exponential moving window of length T, $$\dot{\hat{X}}_p = \frac{1}{T\hat{f}(t, \hat{X}_p; T)}\{p - \theta[\hat{X}_p - X(t)]\}. \qquad (31)$$

In this example p enters the equation for $\hat{X}_p(t)$ explicitly rather than through the initial condition only, as in a general case of Eq. (27). The exponential window is causal, and has an advantageously low computational cost (including low memory requirements) and easy analog implementation. For these reasons this choice of weight function is preferred.

From the PTF output signal, $\hat{X}_p(t)$, can be obtained another approximation, denoted as $\hat{\hat{F}}(t,x;w)$, for the TWCDF (and TWFD) by standard interpolation or extrapolation means (e.g., linear interpolation and extrapolation to enable evaluation of the distribution function approximation at values between ordered pairs $\{(\hat{X}_{p_i}(t),p), i=1\ldots n\}$ that serve as nodes for the distribution approximation).

The PTF output (and the TWCDF estimates) make accessible important information about the level of quantified features present in the specialized time-window defined by the time-weight function. Prior to this invention, none of this information could be obtained in a completely analog system, and the computational cost of deriving this information in digital implementations was significantly more expensive and less efficient.

Step 5: (Optional) Normalize the Signal

The present invention facilitates an optional normalization technique which may be performed at this point, as shown in box 30. The desirability of performing this optional step will depend upon the nature of the signals of interest, particularly their respective scales.

Given any input signal, z(t), and any (possibly time-varying) cumulative distribution function, F(t,x), a new signal, y(t), may be obtained by evaluating the distribution function at the input signal value, i.e., y(t)=F(t,z(t)). This new signal may be referred to as the normalization of signal z with respect to the distribution F.

The signal, y(t), is deemed "normalized" because, no matter what the values/range taken by the input signal, the resulting signal values are always in the interval [0,1]. The flexibility of this normalization technique is that any distribution function and input signal may be utilized (provided only that F is defined so that its second argument is of the same dimension as the input signal), as well as the observation that, for a stationary distribution (i.e., F(t,x)=F(x)) the procedure is a monotonic transformation of the input signal, make this a useful tool for signal analysis.

This normalization technique can be combined with the herein described techniques for approximating the TWCDF of a signal, to enable normalization of an input signal with respect to a time-weighted distribution function of the feature signal of the same (or a different) signal. More specifically, the combination of methods results in the normalized signals $\hat{y}(t)=\hat{F}(t,x(t);w)$ and $\hat{\hat{y}}(t)=\hat{\hat{F}}(t,x(t);w)$.

This normalization technique (together with the method for detecting changes in a time-varying distribution function described elsewhere herein) has been successfully applied, for example, to the problem of automated speech recognition, accurately detecting each occurrence of a particular phoneme in digitally recorded speech.

Step 6: Compare Foreground and Background or Reference Distributions/Densities in Order to Detect and Quantify Changes in Signal Features Referring to FIG. 2, the foreground signal and background or reference signal may now be compared in order to detect or quantify feature changes in the foreground signal. That is, the ability to extract information from (or restrict the influence of information to) different time scales through weighting functions, and the ability to precisely control the set of features under study, allows further use of feature density analysis method as a component of a system for detection and quantification of feature changes. Referring also to FIG. 3, such detection and quantification is accomplished by comparing the PTF outputs (or entire time-weighted feature densities) in the moving foreground window with that of a background or established reference from which a specified change is to be detected.

The method described thus far makes available TWCDF approximates and associated PTF signals for various percentiles. These are determined in part by the time-weight function used in their definition and computation, which describes the way information is weighted and utilized in the production of these approximations. These approximations can be further analyzed and utilized to produce new and highly valuable means for detection and quantification of changes in the feature signal, and therefore in the underlying system that provided the raw signal input.

Generally, the concept is one of comparison between results obtained for different time-weighting of the information provided by the percentile tracking filter outputs or approximations of the TWFD or corresponding TWCDF of the feature signal. One skilled in the art will appreciate that the user may specify two (or more) time-weight functions, $w_1$ and $w_2$, with different characteristic timescales, $T_1$ and $T_2$, respectively, and thereby obtain two sets of PTF outputs and TWCDF approximations:

$\hat{X}_p(t;w_1)$ and $\hat{F}_1(t,x;w_1)$, $\hat{F}_1(t,x;w_1)$ corresponding to timescale $T_1$, and $\hat{X}(t;w_2)$ and $\hat{F}_2(t,x;w_2)$, $\hat{F}_2(t,x;w_2)$ corresponding to timescale $T_2$.

$T_1$ is preferably chosen to be much larger than $T_2$ so that a comparison may be performed of the above quantities, interpreting the former as representing the background or reference information (i.e., obtained from a large time window of past or historical information) and the latter set as being representative of the foreground or more current, test information (i.e., obtained from a small time window of recent information). The existence of a reference for the comparison allows a built-in type of normalization that ensures comparison of "apples to apples" in the resulting analysis. The reference information need not necessarily be continually updated (the time between updates could, e.g., be proportional to the timescale analyzed), or a constant set of information (e.g., a constant, C, and fixed distribution, $F_{ref}(t,x)$) may be used as a reference for the comparison with $\hat{X}_p(t;w_2)$ and $\hat{F}_2(t,x;w_2)$ or $\hat{F}_2(t,x;w_2)$ respectively. One skilled in the art will recognize that any of the standard techniques for statistical analysis of data and for comparison of distributions or densities can also now be applied for time-dependent quantification of the signal and its changes.

The wealth of comparisons that may be performed between the PTF outputs are well known to those skilled in the art of signal analysis. Although such outputs were not available prior to the present invention, there are numerous known techniques for comparison of test signals to reference signals that may be employed to these newly available PTF outputs. A typical example (utilizing the type of comparison employed in the successful detection algorithm disclosed in U.S. Pat. No. 5,995,868) involves computing a ratio of the foreground and background outputs, e.g., $$r(t) = \frac{\hat{X}_p(t;w_2)}{\hat{X}_p(t;w_1)}, \qquad (33)$$

and then comparing the resulting ratio to a threshold or reference value that, when reached, signifies occurrence of the change that was to be detected.

Comparisons between test and reference time-weighted densities and distributions of the feature signal have been invented to allow the user to quantify differences and detect a wide array of changes in these distributions with great sensitivity and specificity. Further, these comparisons (and those mentioned above for the PTF) have also been implemented in analog form and in highly efficient digital form.

A time-varying signal, referred to as a $\Lambda$-estimator, is defined to quantify the difference between distributions by functioning as a type of distance measure between them as $$\Lambda(t;W,G) = \Lambda(F_1(t,x;w), F_2(t,x;w)) \qquad (34)$$

$$= \int_{-\infty}^{\infty} W(F_1(t,y;w))G(F_1(t,y;w) - F_2(t,y;w))\,dF_1(y)$$

$$= \int_{-\infty}^{\infty} W(F_1(t,y;w))G(F_1(t,y;w) - F_2(t,y;w))f_1(y)dy$$

for some percentile weighting function, W, and some spatial weighting function, G.

The $\Lambda$-estimator, through choice of weighting functions, is able to quantify a wide array of differences in the two distributions being compared.

For example, consider an estimator of the differences between the foreground and background distributions as follows:

$$\Lambda = \qquad (35)$$

$$\lambda_\pm = \int_{-\infty}^{\infty} W[F_{bg}(x)][F_{bg}(x) - F_{fg}(x)]\theta\{\pm[F_{bg}(x) - F_{fg}(x)]\}\,dF_{bg}(x),$$

where the percentile weighting function W(z) is such that $$\int_0^1 zW(z)\,dz = 1,$$

and a pair of spatial weighting functions (giving rise to a pair of estimators, $\lambda_\pm(t)$,resp.) is given by $G_\pm(x)=x\theta(\pm x)$. The above parameters compute weighted distance between the background and the foreground for specific cases of $F_{fg}<F_{bg}$ and $F_{fg}>F_{bg}$ for $\lambda+$ and $\lambda-$ respectively.

Computing $\lambda_\pm$ estimators becomes especially easy if the weighting function W(x) is a delta function, $$W(x) = \frac{1}{p}\delta(x-p).$$

Thus Eq. (35) reduces to $$\lambda \pm = \left[1 - \frac{1}{p}F_{fg}(x_p)\right]\theta\left\{\pm\left[1 - \frac{1}{p}F_{Fg}(x_p)\right]\right\}, \quad (36)$$

where $x_p$ is such that $F_{bg}(x_p)=p$, i.e., the output of the PTF for $p^{th}$ percentile. Using the fact that $F_{fg}[x_p(t)]=\langle\theta[x_p(t)-X(s)]\rangle_{T_{fg}}$, Eq. (36) becomes $$\lambda \pm (t) = \frac{1}{p}\left[p - \langle\theta[x_p(s) - X(s)]\rangle_{T_{fg}}\right]\theta\left\{\pm\left[p - \langle\theta[x_p(s) - X(s)]\rangle_{T_{fg}}\right]\right\} \quad (37)$$

where we replaced $x_p(t)$ by $x_p(s)$ in the assumption that $T_{bg} \gg T_{fg}$, and therefore $x_p(t)$ changes slowly with respect to $X(t)$.

For example, consider a simple mix of two signals with $$W(x) = 2\delta\left(x - \frac{1}{2}\right),$$

$F_{bg}(x)=F(x)$, and $$F_{fg}(x) = (1-\alpha)F(x) + \alpha F\left(\frac{x}{q}\right).$$

That is, the foreground window contains a mix of two signals such that the ratio of their mean values is q. Then $$\lambda \pm = \alpha\left[1 - 2F\left(\frac{x_{\frac{1}{2}}}{q}\right)\right]\theta[\pm(q-1)], \quad (38)$$

where $x_{1/2}$ is such that $$F\left(x_{\frac{1}{2}}\right) = \frac{1}{2},$$

i.e., the background median. If $\lim_{x \to 0}F(x)=0$, and $$q + \frac{1}{q} \gg 1, \text{ then } 1 - 2F\left(\frac{x_{\frac{1}{2}}}{q}\right) \approx \text{sign}(q-1) \text{ and} \quad (39)$$

$$\lambda \pm \approx \pm\alpha\theta[\pm(q-1)].$$

Thus the values of $\lambda\pm$ become a measure of fraction of the second component in the foreground window.

The invariance of the $\Lambda$ estimators given by Eq. (34) to a monotonic transformation (function) of the signal $f[X(t)]$, e.g., $a>b \Rightarrow f(a)>f(b)$), allows simplification of computations by rescaling the signal to a convenient range, and makes the change detection invariant to non-linear amplification of the raw signal. In combination with a signal preprocessing system which provides methods for taking a raw input signal, measuring desired features or properties of that signal, then transforming the output into (several) signals of amplitudes which characterize the levels of the particular features under study as they evolve over time, the above mentioned tools enable rapid, efficient, and reliable detection of changes in these specific features and tracking of their time evolution.

Figure 2:
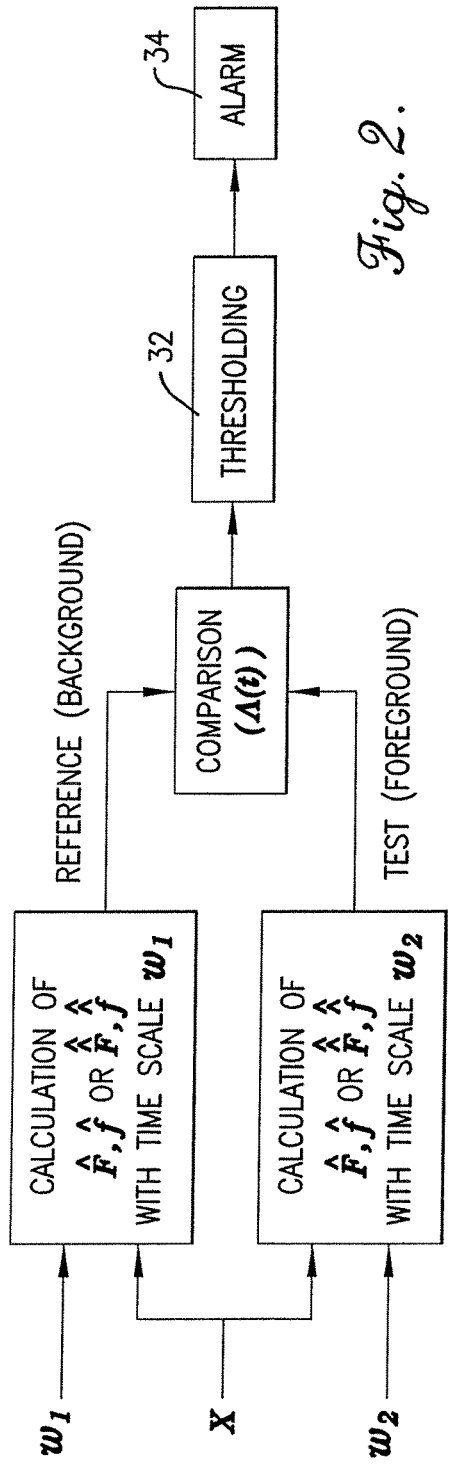
FIG. 2 is a block diagram illustrating a second portion of steps involved in performing a preferred embodiment of the present invention.
Figure 3:
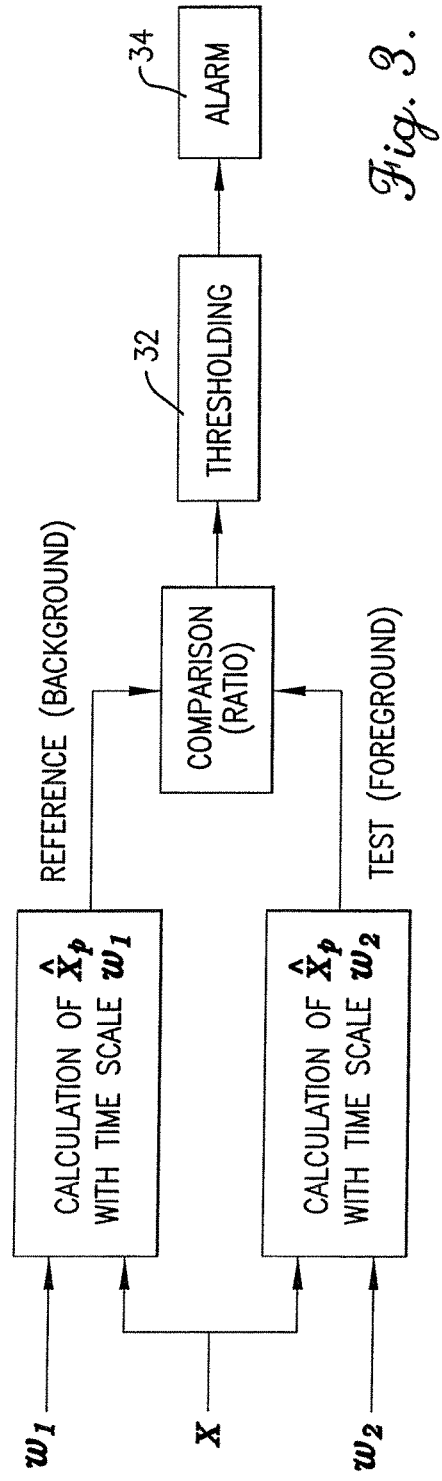
FIG. 3 is a block diagram illustrating a third portion of steps involved in performing a preferred embodiment of the present invention.

In both FIGS. 2 and 3, thresholding of the resulting comparison output is performed, as shown in box 32, in order to detect feature changes exceeding a pre-defined value. Where such feature changes are detected, an alarm, whether visual, audible, or otherwise, may be communicated, as shown in box 34.

Step 7: (Optional) Predict Future Changes

Lastly, the present invention's ability to rapidly and accurately detect changes in certain features of an input signal can be used to predict future changes in cases when the detected changes are associated with an increased likelihood of these future changes. For example, when applied to seismic signals, the method can enable prediction of an earthquake or volcanic eruption; when applied to meteorological signals, the method can enable prediction of severe weather; when applied to financial data, the method can enable prediction of an impending price change in a stock; when applied to brain waves or heart signals, the method can enable prediction of an epileptic seizure or ventricular fibrillation; and when applied to brain wave or electromyographic signals, the method can enable prediction of movement of a body part.

Example: Financial Analysis

Figure 4:
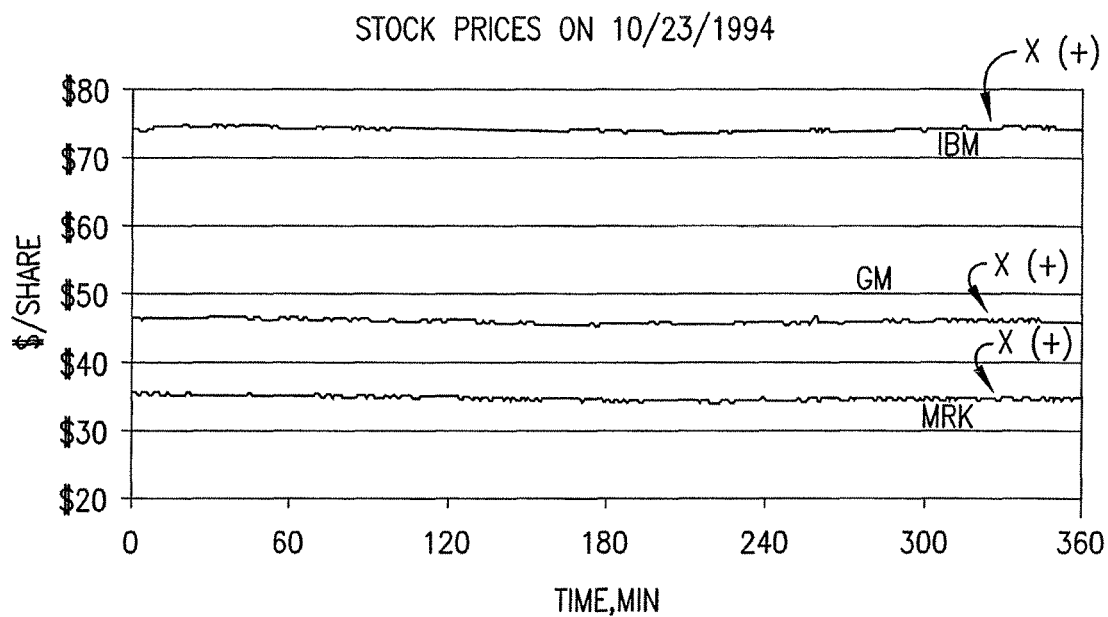
FIG. 4 is a graph of an exemplary raw input signal, x(t), as might be received for analysis by a preferred embodiment of the present invention.

In an exemplary illustration of application of the present invention to financial analysis, a three-dimensional raw input signal, x(t), is received such that, as shown in FIG. 4, x(t) is the price at time t of three stocks (IBM, GM, and MRK) during a 360 minute period on Oct. 23, 1994.

Figure 5:
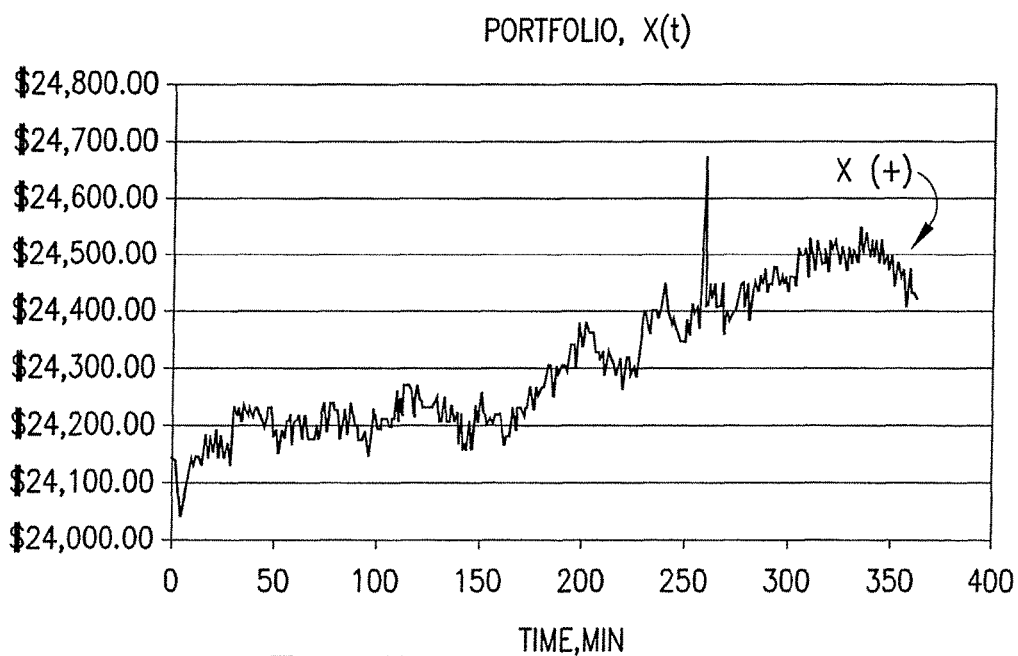
FIG. 5 is a graph of a feature signal, X(t), resulting from preprocessing the raw input signal shown in FIG. 4.

Pre-processing is then performed on x(t) to yield a feature signal, X(t), as shown in FIG. 5, such that X(t) is the value of a portfolio at time t comprising the three stocks of interest: X(t)=300*GM+100*IBM+80*MRK.

Figure 6:
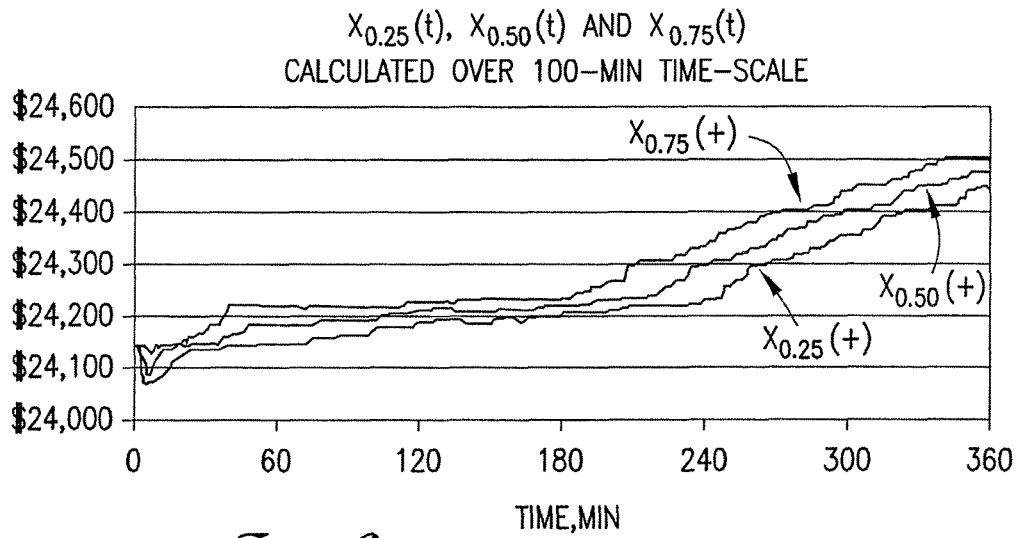
FIG. 6 is a graph showing the calculated 0.25, 0.50, and 0.75 percentiles of the feature signal shown in FIG. 5.
Figure 7:
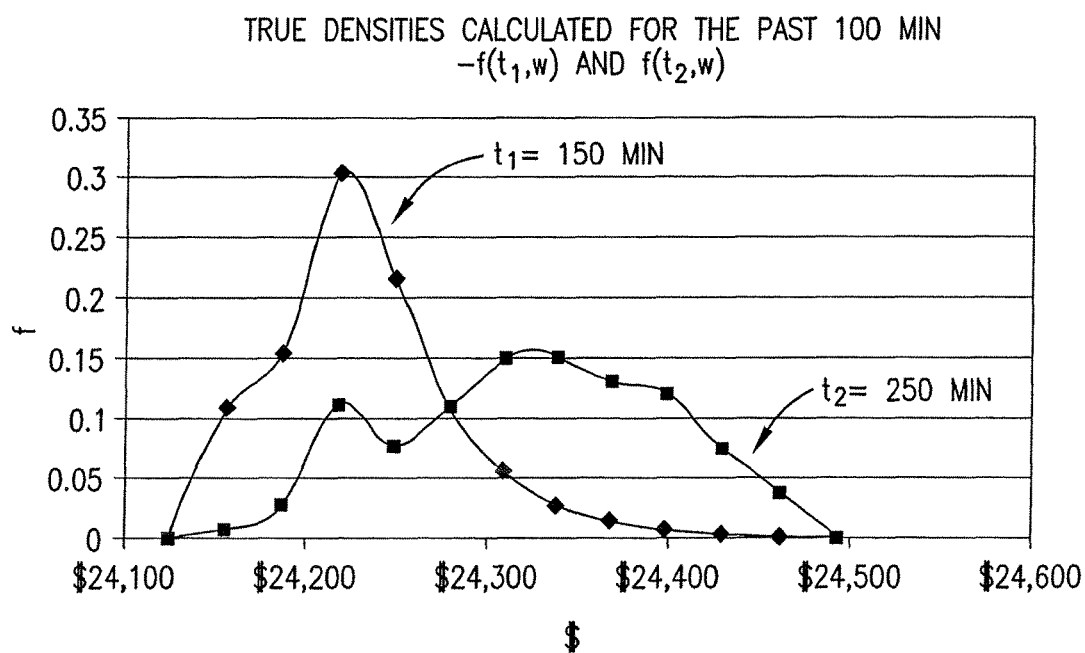
FIG. 7 is a graph showing the true feature density, $f(t,w)$ of the feature signal shown in FIG. 5 calculated at times $t_1$ and $t_2$.
Figure 8:
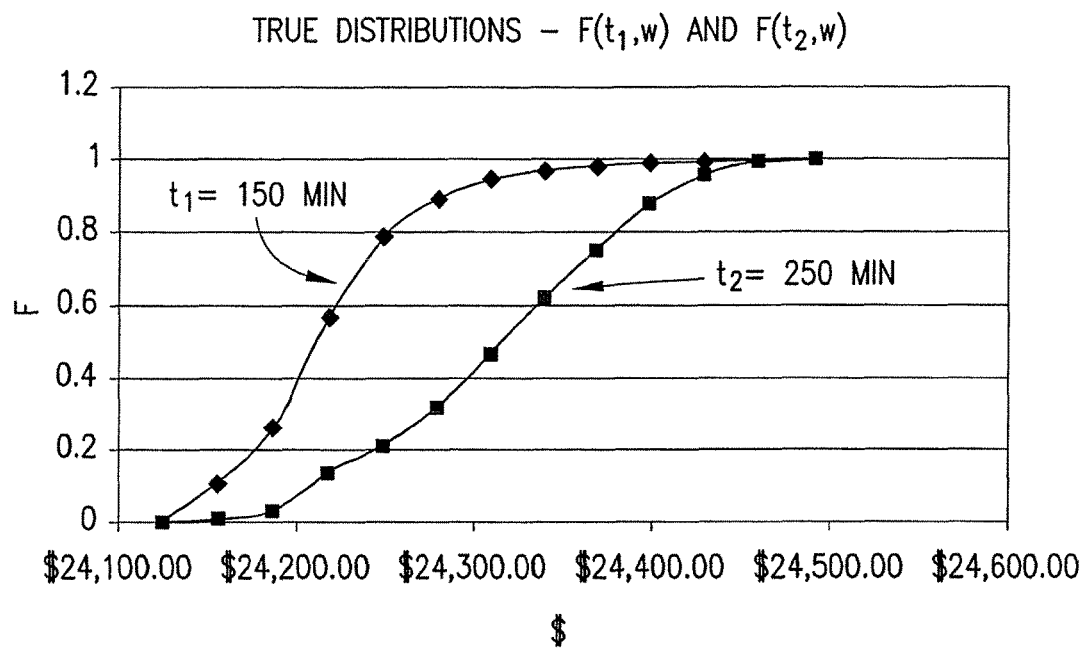
FIG. 8 is a graph showing the true feature distribution, $F(t,w)$, of the feature signal shown in FIG. 5 calculated at times $t_1$ and $t_2$.

Next, as time, t, evolves, the time-weight function, w(t,s), is defined for use at each time point. In the present example, w is defined so that the time-weight is a moving square window of length T=100 minutes. In practice, more complicated time-weights could be used that include a dependence upon an auxiliary signal such as oil prices and supplies which may have a direct impact in GM stock prices by influencing consumer preferences and cash availability. Another time-weight, for example is the average temperature across the U.S. for the past week (thus incorporating information that could have an effect on the feature signal if, e.g., a freeze altered the price of wheat futures or heat wave altered the price of California energy companies) that could directly or indirectly affect these or other stocks. The true 0.25, 0.50, and 0.75 percentiles are shown in FIG. 6 as, respectively, $X_{0.25}(t)$, $X_{0.50}(t)$, and $X_{0.75}(t)$. The true feature density, $f(t,w)$, and distribution, $F(t,w)$, are calculated from the data at two different times, $t_1$ and $t_2$, as shown in FIGS. 7 and 8. The parameters are calculated for a time-scale of 100 minutes.

Figure 9:
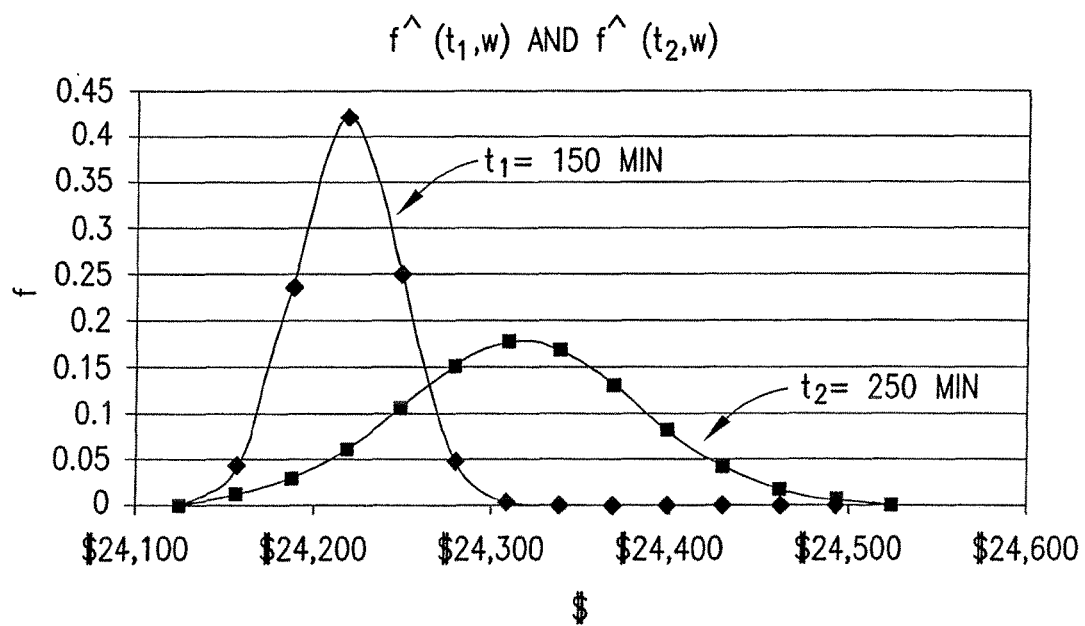
FIG. 9 shows a graph of an evolving first approximation of the time-weighted feature density of the feature signal shown in FIG. 5, calculated at times $t_1$ and $t_2$.
Figure 10:
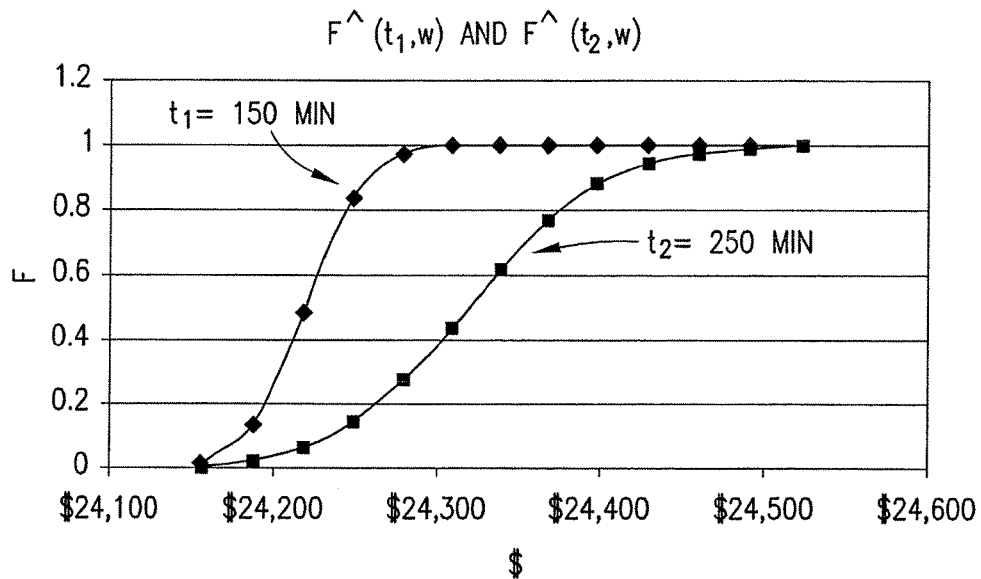
FIG. 10 shows a graph of an evolving first approximation of the time-weighted distribution function of the feature signal shown in FIG. 5, calculated at times $t_1$ and $t_2$.

Next, the feature signal and time-weight are used to compute/update an evolving approximation to the time-weighted density and corresponding distribution function of the feature signal: $\hat{f}(t,x;w)$ and $\hat{F}(t,x;w)$. In the present example, $\hat{f}(t,x;w_1)$ and $\hat{F}(t,x;w_1)$ are evaluated assuming a Gaussian (normal) density approximation (bell-shaped) for the data over the past 100 minutes. These approximations can be compared to the true distributions shown in the previous figure. Again, these were evaluated at two different times, $t_1$ and $t_2$, as shown in FIGS. 9 and 10.

Figure 11:
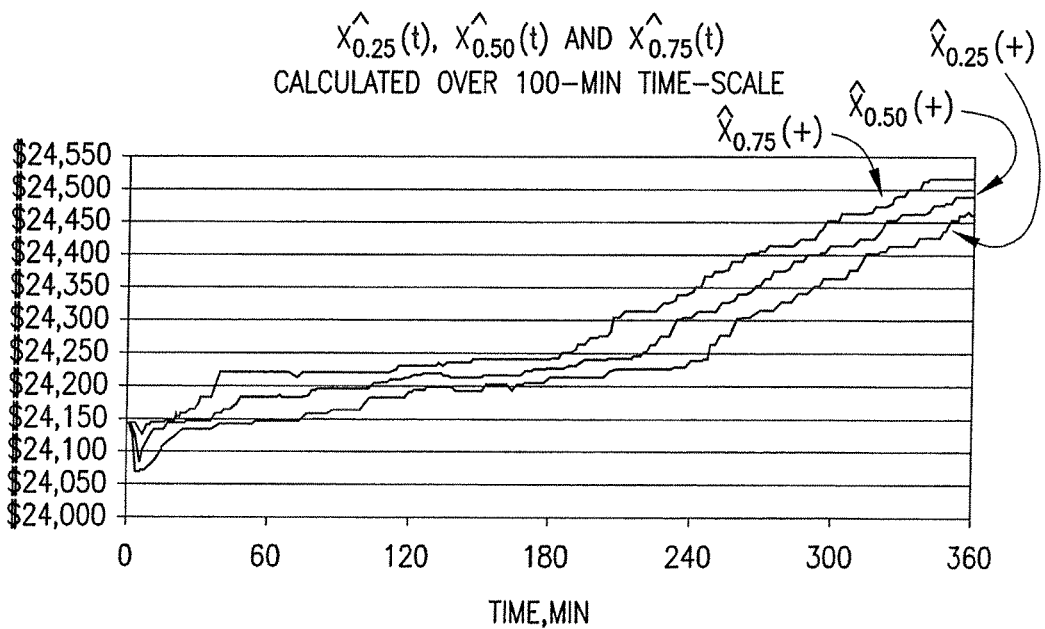
FIG. 11 is a graph showing calculated percentile tracking filter outputs for 0.25, 0.50, and 0.75 percentiles of the feature signal shown in FIG. 5.

The feature signal, a specified set of one or more percentile values, p, and approximations $\hat{f}(t,x;w)$ and $\hat{F}(t,x;w)$ are then used to compute/update the PTF output, $\hat{X}_p(t;w)$. It will be appreciated that p may be a vector of multiple percentiles, as in this example where p=[0.25, 0.50, 0.75]. The PTF output, $\hat{X}_p(t;w)$, is shown in FIG. 11.

Figure 12:
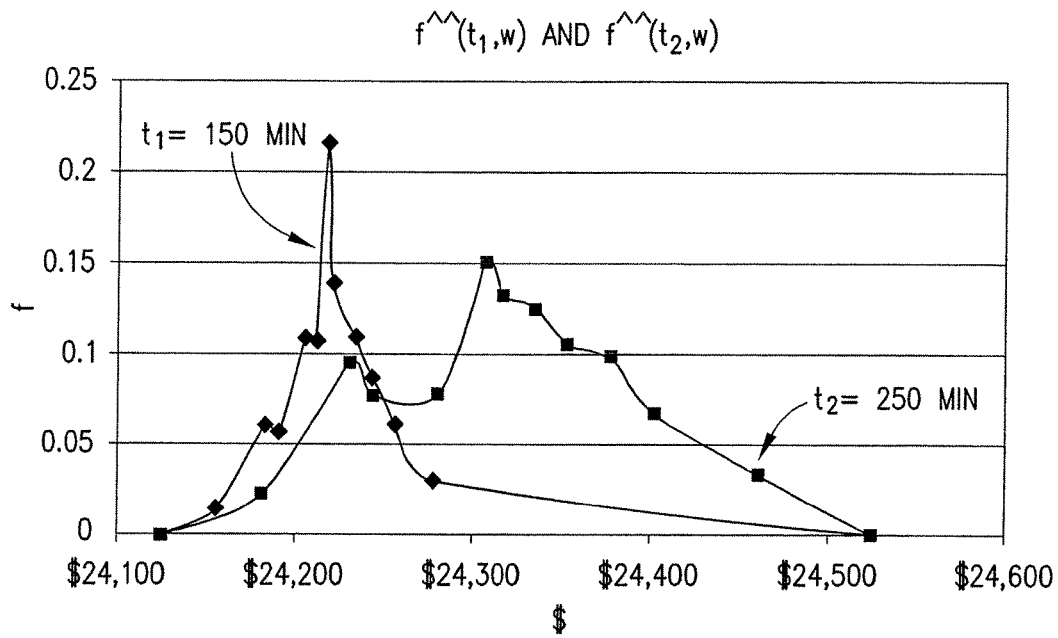
FIG. 12 shows a graph of an evolving second approximation of the time-weighted feature density of the feature signal shown in FIG. 5, calculated at times $t_1$ and $t_2$.
Figure 13:
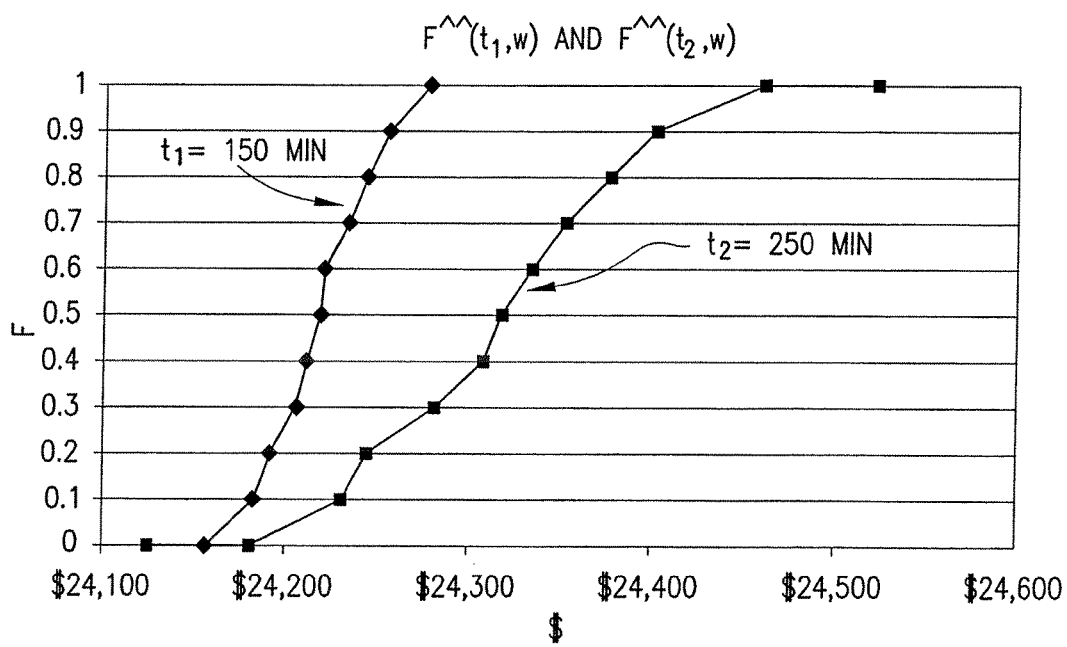
FIG. 13 shows a graph of an evolving second approximation of the time-weighted distribution function of the feature signal shown in FIG. 5, calculated at times $t_1$ and $t_2$.

An interpolation/extrapolation scheme is then used to compute/update a second set of (evolving) approximations to the time-weighted density and corresponding distribution function of the feature signal, $\hat{\hat{f}}(t,x;w)$ and $\hat{\hat{F}}(t,x;w)$. In the present example, $\hat{\hat{f}}(t,x;w_1)$ and $\hat{\hat{F}}(t,x;w_1)$ were determined using the outputs of the PTF by linear interpolation. These were again evaluated at the times, $t_1$ and $t_2$, as shown in FIGS. 12 and 13.

Figure 14:
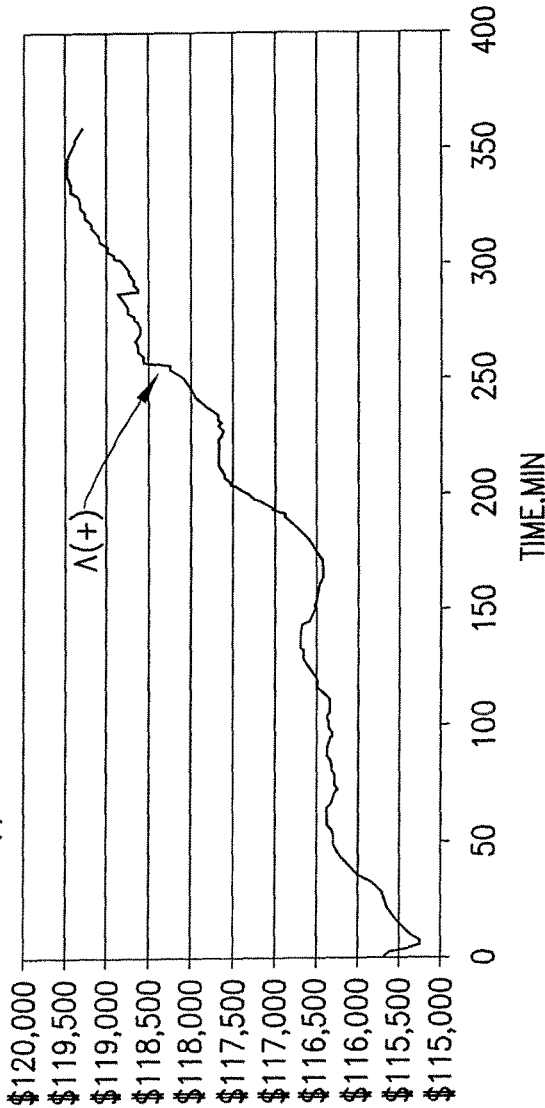
FIG. 14 shows a graph of a $\Lambda(t)$ measured from the feature signal shown in FIG. 5.

Then the PTF output and approximations to the time-weighted density/distribution of the feature signal are analyzed to detect, quantify, or predict changes in the system that produced the raw signal. This analysis may consist, for example, of establishing or computing a reference against which to compare the information being generated. One preferred approach is to use a fixed reference value and a fixed density/distribution and compare them to the PTF and the density/distribution approximations, respectively. A second preferred approach involves performing the prior method steps simultaneously with two differing choices of time-weight function, one to establish a reference PTF and density/distribution approximation and the other to generate a test PTF and density/distribution approximation, then comparing the two resulting sets of information. Described above is a method for comparing two PTF outputs (e.g., computing their ratio) and for comparing test-to-reference distributions (Λ-estimators). The ratio and/or Λ-estimators are used to compare the feature content in one time-window/scale to another. Changes may be detected, e.g., by applying thresholds to either ratio and/or Λ-estimators. In the present example, the above calculations were performed on short time-scale of 100 min. The long time-scale calculations were performed using the portfolio variations starting from 1980 until 2001 with a time-scale of T=1 year. This was taken as reference for the calculation of the Λ parameter. Thus, a simple difference between $\hat{\hat{F}}(t)$, evaluated for a T=100 min and $\hat{\hat{F}}_{REF}$, evaluated with a time-scale of T=1 year was used for Λ(t), as shown in FIG. 14.

It should be noted that the Λ(t) signal on the 100 minute time scale was unaffected by the more brief outlier spike that occurred in the feature signal approximately 260 minutes into the day's trading.

Lastly, once features of the financial system from which the raw signal was measured have been detected and quantified, the output may be utilized. One such use of this information is signal normalization (of any signal) with respect to any of the distribution approximations made available by the present invention. Another use involves prediction of future changes if it happens that the detected changes are associated with an increased likelihood of certain future signal changes.

In the present example, the portfolio value on the particular day did not demonstrate any significant change over the background distribution, so the owner may have simply decided to maintain his holdings at that time.

COMPUTER PROGRAM

A computer program listing appendix containing the source code of a computer program operable to implement the above-described method is incorporated herein by reference and appended hereto. The computer program comprises a combination of source code segments corresponding to the steps of the method. The combination of computer code segments may be stored on any computer-readable media, such as magnetic disk, magnetic tape, or CD-ROM, and executed by a conventional personal computer or similar computing device. As will be appreciated by one with skill in the programming arts, the combination of source code segments may be written in any suitable programming language.

During execution, one or more of the combination of source code segments will require input, such as the raw input signal, which may be provided by any suitable device, such as an oscilloscope or transducer, or application, such as a spreadsheet, the nature of which will depend upon the nature of the input.

SYSTEM

Figure 15:
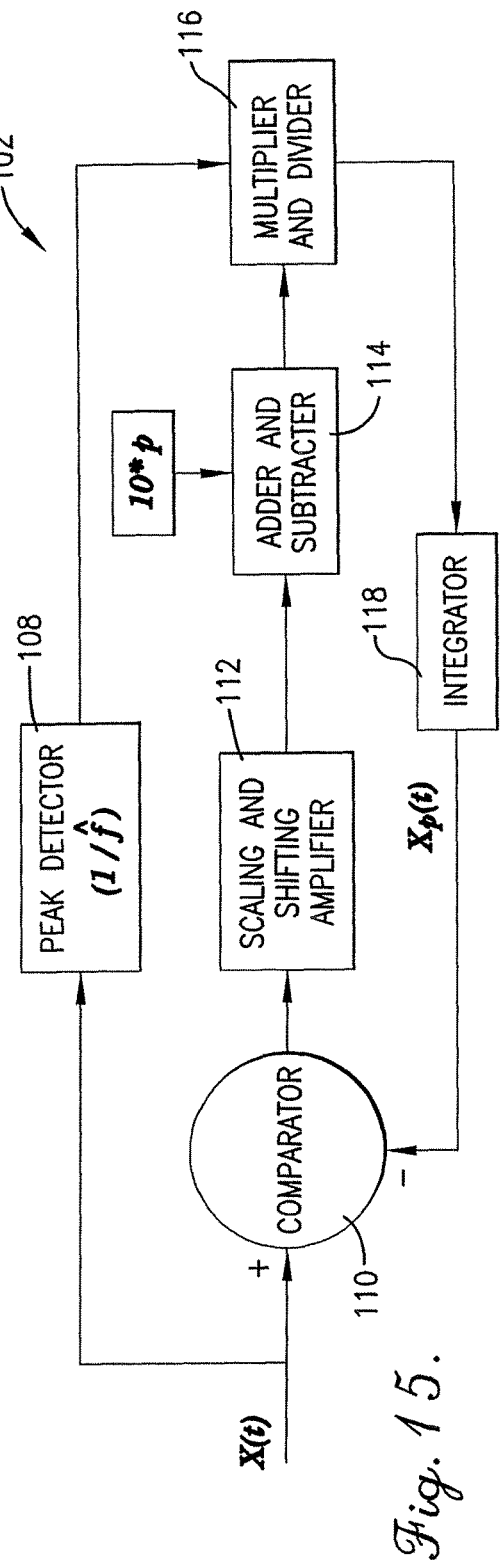
FIG. 15 is a block diagram of a preferred embodiment of an analog implementation of a percentile tracking filter component of the present invention.
Figure 16:
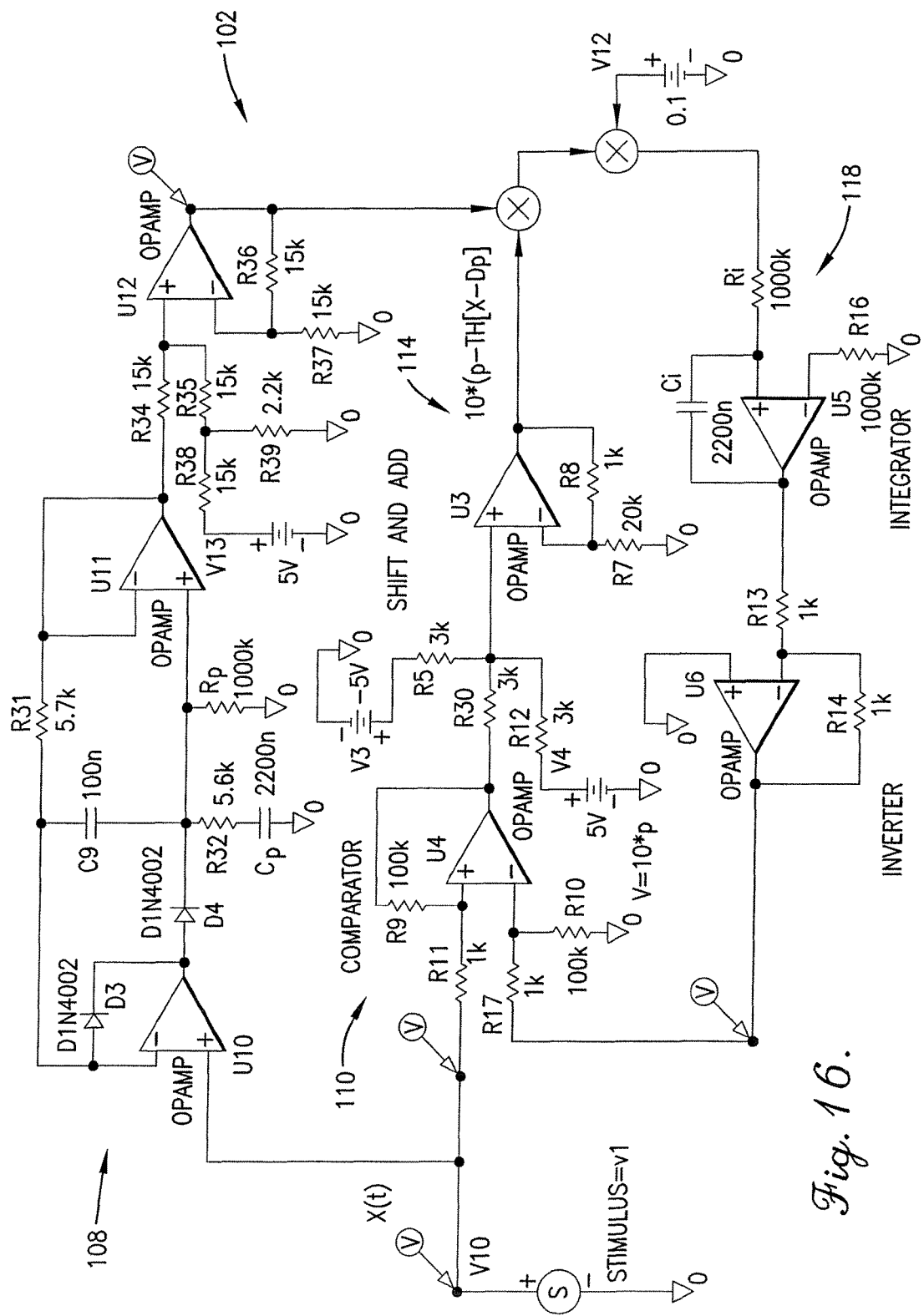
FIG. 16 is a detailed circuit schematic of the percentile tracking filter component shown in FIG. 15.
Figure 17A:
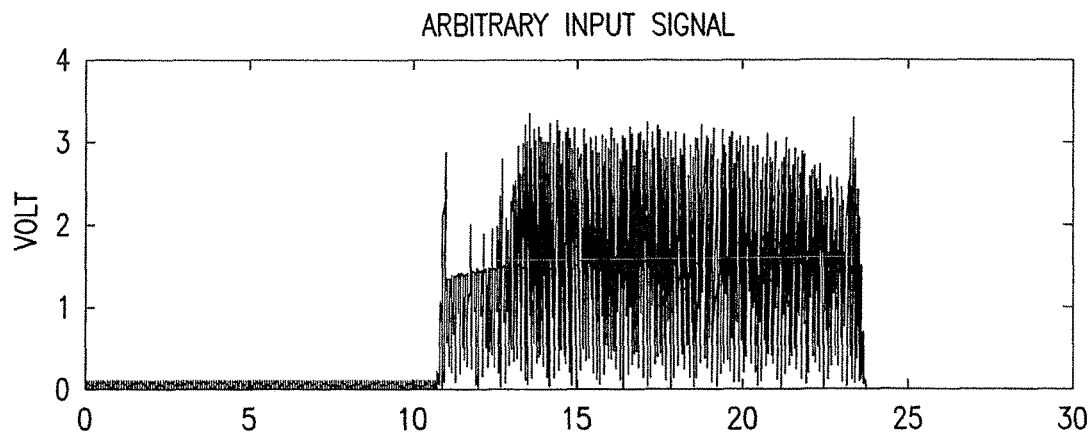
FIG. 17A shows an exemplary feature signal that for analysis by the present invention.

FIGS. 15 and 17 show block diagrams of a preferred analog system 100 operable to implement the above-described method. FIGS. 16 and 18 show detailed circuit schematics of a preferred embodiment of the analog system 100 shown described generally in FIGS. 15 and 17. The analog system 100 comprises two major components, an analog PTF circuit 102 and an analog Lambda circuit 104. This implementation is based upon a recognition that the use of approximations in determining feature density facilitate tracking of the percentile in real-time with minimal errors. The use of a uniform density distribution makes the implementation simpler by an order of magnitude over implementations involving distributions with exponentiation, while providing and output that closely tracks the actual median obtained by sorting. The implementation outputs the percentile value of the input signal in real time while retaining the controllability and flexibility of a digital algorithm.

Referring first to FIG. 15, the analog PTF circuit 102 broadly includes a peak detector stage 108; a comparator stage 110; a scaling and shifting amplifier stage 112; an adder stage 114; a multiplier and divider stage 116; and an integrator stage 118.

The peak detector stage 108 determines the peak of an incoming signal. For a uniform distribution, the density function $f(t, w)$ is given by $1/(b-a)$, where $b(t)$ and $a(t)$ are the maximum and the minimum of the signal respectively. Thus, for a=0 (this can be achieved using the optional preprocessing step), the peak detector stage 108 gives $1/\hat{f}$.

The comparator stage 110 performs the step of computing: $\theta\lfloor X(s)-X_p(S)\rfloor$. The output of the comparator stage 110 is a voltage equal to a saturation voltage (±15 V) of an amplifier component of the comparator stage 110.

The scaling and shifting amplifier stage 112 brings the voltage to 0-10 V. This enables direct subtraction from the input 10*p in the adder 114.

The adder stage 114 subtracts the output of the scaling and shifting amplifier stage 112 from 10*p. Thus the output of the adder stage 114 is $10*(p-\theta\lfloor X(s)-X_p(s)\rfloor)$.

The multiplier and divider stage 116 multiplies the output of the adder stage 114 and divides the result by 10. Thus the output of this stage 116 is $$\frac{1}{\hat{f}}(p - \theta[X(s) - X_p(s)]),$$

which is $T\dot{X}_p$.

The integrator stage 118 has an input-output relationship defined by the following equation:

$$V_o = \frac{1}{RC} \int_{-\infty}^{t} V_i \, dt,$$

where $V_i$ and $V_o$ are the input and the output respectively. Thus the output of this stage 118 is $$\frac{1}{RC} TX_p(t).$$

Choosing proper values for R and C will give us an output that is equal to $X_p(t)$.

Referring also to FIG. 16, the peak detector stage 108 has a natural exponential forgetting factor due to discharging of the capacitor $C_p$. The time-window of exponential forgetting for the peak can be controlled by varying the resistor $R_p$. The time-window over which the percentile is calculated, is controlled by the integrator stage 118. Resistor $R_i$ and a capacitor $C_i$ of the integrator stage 110 control the time factor T. By tuning these parameters, $R_p$, $C_p$, $R_i$ and $C_i$, the PTF circuit 102 can be tuned to approximate a percentile filter with specific properties. For example, by choosing the following values: $R_p$=1.0MΩ, $C_p$=2.2 μF, $R_i$=1.0MΩ, and $C_i$=2.2 μF, there is achieved an exponential forgetting time constant of 2.2 seconds and a percentile time-window of 2.2 seconds.

Figure 17B:
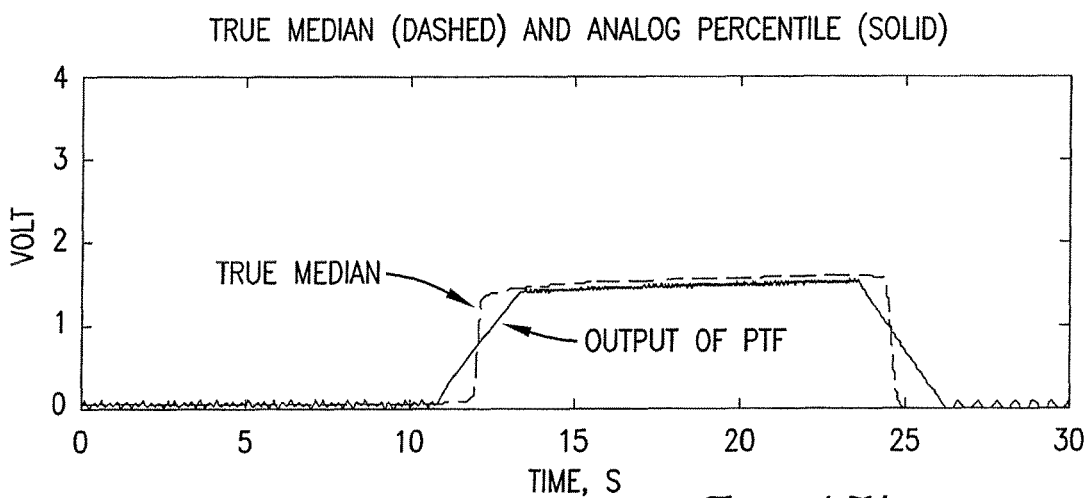
FIG. 17B shows an output of the detailed circuit schematic shown in FIG. 16 and a true median output associated with the feature signal of FIG. 17A.
Figure 18:
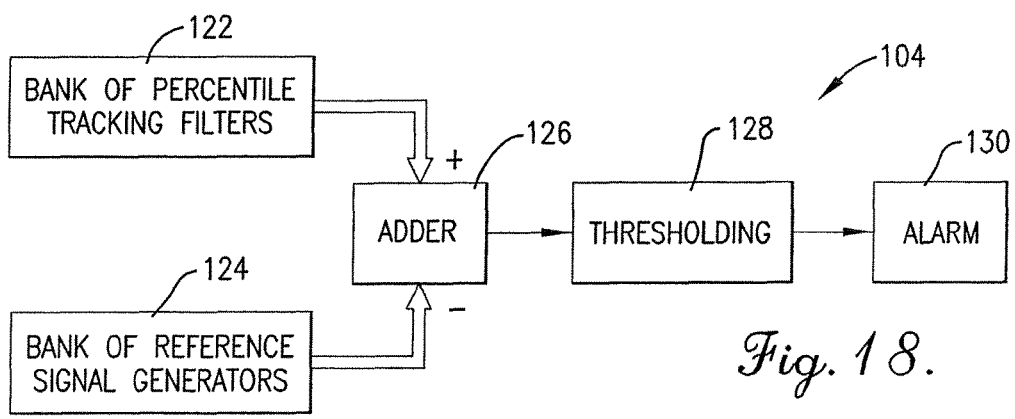
FIG. 18 is a block diagram of a preferred embodiment of an analog implementation of a Lambda estimator component of the present invention.

The output of the PTF circuit 102 with these parameters to an example feature signal input (shown in FIG. 17A) is shown in FIG. 17B. Also shown in FIG. 17B is the true median obtained by performing a heap sort of sliding 2.2-second window on the input data. Note that the PTF circuit 102 responds to changes in the signal faster than the true median. This is because the true N-sample median does not respond until N/2 (or [N+1]/2 if N is odd) samples have passed through the filter. However, due to the implementation of the PTF using exponential forgetting, it responds to changes almost instantaneously. This property of the PTF is valuable when attempting to detect rapid signal amplitude changes.

Referring to FIG. 18, the analog Lambda circuit 104 broadly comprises a bank 122 of PTF circuits 102; a bank 124 of reference signals; an adder stage 126; a thresholding stage 128; and an alarm stage 130.

The bank 122 of PTF circuits 102 comprises one or more PTF circuits 102, each applied on the original signal, x(t) or feature signal X(t). The output of this bank 122 is the calculation of $F_{fg}$ (Eq. 35).

The bank 124 of reference signals can be PTF circuits 102 applied to the original raw input or to the feature signal. In such a case, the reference signals are typically generated by using large time-scales during the integration step of the PTF operation. Otherwise, the reference signals can be simple constant voltage sources. There is a reference signal corresponding to each of the PTF circuits 102 in the above bank 122. The output of this bank 124 is the $F_{bg}$.

The adder stage 126 adds the output of the bank 122 of PTF circuits 102 to the negative output of the bank 124 of reference signals. This stage 126 can also selectively amplify or attenuate the result of each subtraction. Thus the output of the adder stage 126 is a summation of the weighted difference between the PTF circuit 102 output signal and the reference signal, which is the Lambda parameter:

$$\Lambda(t) = \Sigma w(t,x)(F_{fg}(t,x) - F_{bg}(t,x)). \tag{40}$$

w(t,x) can be selected to give a parameter of choice.

The thresholding stage 128 detects increases in the Lambda parameter beyond a particular threshold. This stage 128 may be implemented as a comparator.

The alarm stage 130 communicates threshold crossing detected by the thresholding stage 128, and can be implemented as in many different ways, from a simple light (or beep) to a complicated circuit that can perform a sequence of steps, such as a computer that can perform some predetermined operation.

Figure 19:
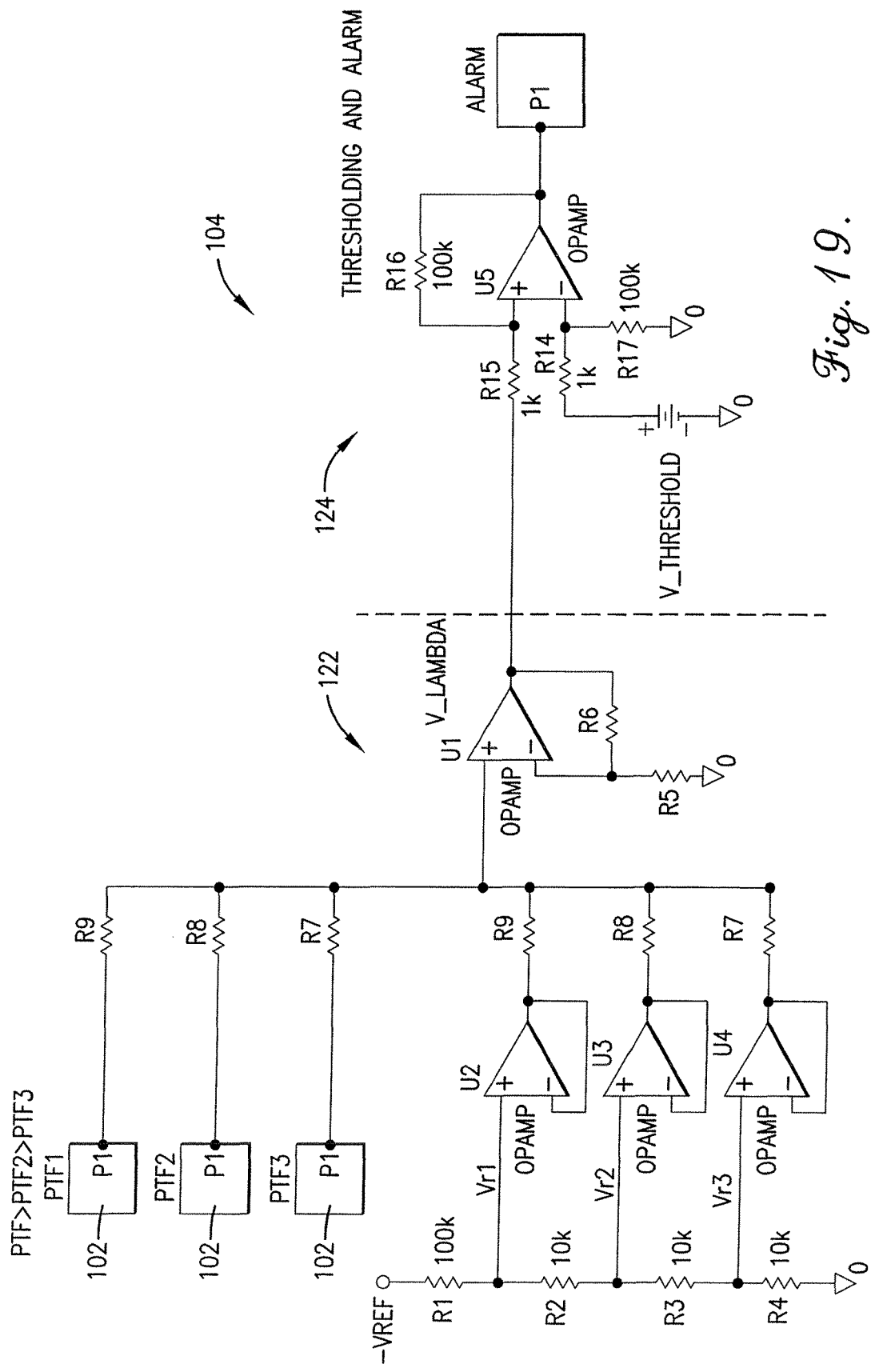
FIG. 19 is a detailed circuit schematic of the Lambda estimator component shown in FIG. 18.

Referring also to FIG. 19, an analog Lambda circuit is 104 shown operable to compute the Λ parameters from the percentiles of the input signal and constant reference signals. The inputs to the analog Lambda circuit 104 are the outputs $PTF_1$, $PTF_2$, and $PTF_3$ provided by parallel PTF circuits 102. $PTF_1$, $PTF_2$, and $PTF_3$ correspond to the $p_1$, $p_2$ and $p_3$ percentile of the input signal such that $p_1 > p_2 > p_3$. The reference signals in the circuit 104 are $Vr_1$, $Vr_2$, and $Vr_3$ such that $Vr_1 > Vr_2 > Vr_3$. The Lambda circuit 104 comprises first and second stages 134,136, wherein the first stage 134 is operable to provide the calculated Λ parameter, and the second stage 136 is operable to perform threshold detection and alarm.

The following equations hold for the Lambda circuit 104 shown:

$$V_\Lambda = R_p \left(1 + \frac{R_6}{R_5}\right)\left[\frac{PTF_1 - Vr_1}{R_9} + \frac{PTF_2 - Vr_2}{R_8} + \frac{PTF_3 - Vr_3}{R_7}\right], \tag{41}$$

Where $$R_p = \frac{R_7 R_8 R_9}{R_7 R_8 + R_8 R_9 + R_7 R_9}. \tag{42}$$

The Lambda circuit 104 can be tuned to output a particular parameter by changing the values of resistances $R_5$-$R_9$. For example, if the circuit 104 is to respond to changes in the $p_1$ percentile (say the $75^{th}$ percentile), then the gain of that particular input line can be increased while the other two input lines can be attenuated. In the second stage 136, this voltage can be compared to a specific threshold and an alarm can be triggered.

The present invention, as described herein, provides computationally efficient characterization of temporally-evolving densities and distributions of signal features of arbitrary-type signals in a moving time window by tracking output of order statistic (e.g., percentile, quantile, rank-order) filters. As noted, the present invention's ability to rapidly and accurately detect changes in certain features of an input signal can also enable prediction in cases when the detected changes are associated with an increased likelihood of certain of future signal changes.

Although the invention has been described with reference to the preferred embodiment illustrated in the attached drawings, it is noted that equivalents may be employed and substitutions made herein without departing from the scope of the invention as recited in the claims. Those skilled in the art will appreciate, for example, that although described herein for use with a continuous-time signal, time-weighting can be equally well applied to a discrete-time signal. Thus, the present invention can be implemented in both digital and analog forms.

One skilled in the relevant art will also recognize that any sequence of data, one- or multi-dimensional, resulting from any measurement, may be used as a signal in the present invention. This extends the applicability of the invention beyond the most commonly used definition of a signal, in which the data is parameterized by an index, t, that is interpreted as a time variable, to allow t to be any element of an ordered set. In this event, t is interpreted simply as an index that determines the order in which the data appears in the list, {x(t)}, or its structure. This enhances the understanding of how the invention may be utilized in the analysis of lists or sequences. Specific illustrative examples include analysis of word lists such as those found in a document, enabling the quantification of document content, useful, e.g., in electronic search engine applications; as well as analysis of biologic sequences, structures, or compounds at the molecular, microscopic, or macroscopic level, useful, e.g., in comparison of genetic makeup of a sample to a reference. Similar applications exist to non-biologic sequences, structures or compounds.

Having thus described the preferred embodiment of the invention, what is claimed as new and desired to be protected by Letters Patent includes the following:

1. A medical device including a power source for detecting an epileptic seizure, the medical device configured to implement a method including:
   (a) receiving via one or more processors a heart signal from a patient;
   (b) determining via the one or more processors a heart signal feature from the heart signal;
   (c) determining via the one or more processors a first percentile tracking filter estimate from the heart signal feature in a foreground time window;
   (d) determining via the one or more processors a second percentile tracking filter estimate from the heart signal feature in a background time window;
   (e) comparing via the one or more processors a foreground data to a background data;
   (f) detecting via the one or more processors the epileptic seizure based on the comparison of the foreground data to the background data; and
   (g) in response to the detecting of the epileptic seizure, providing via the one or more processors an output indicative of the detection of the epileptic seizure;
   wherein at least one of the first percentile tracking filter estimate and the second percentile tracking filter estimate is updated using a difference equation, wherein the difference equation updates the at least one of the first percentile tracking filter estimate and the second percentile tracking filter estimate based on a comparison of a heart signal feature status versus a most recent percentile tracking filter estimate status where the comparison determines a first state, a second state, and a third state, wherein the difference equation updates the at least one of the first percentile tracking filter estimate and the second percentile tracking filter by incrementing the at least one of the first percentile tracking filter estimate and the second percentile tracking filter estimate by a first non-negative value based on the first state where the first state is that the heart signal feature is greater than a most recent percentile tracking filter estimate, wherein the difference equation updates the at least one of the first percentile tracking filter estimate and the second percentile tracking filter estimate by decrementing the at least one of the first percentile tracking filter estimate and the second percentile tracking filter estimate by a second non-negative value based on the second state where the second state is that the heart signal feature is below the most recent percentile tracking filter estimate; and
   wherein the difference equation updates the at least one of the first percentile tracking filter estimate and the second percentile tracking filter estimate by leaving the at least one of the first percentile tracking filter estimate and the second percentile tracking filter estimate unchanged based on the third state where the third state is that the heart signal feature value is equal to the most recent percentile tracking filter estimate;
   wherein the utilization of the first percentile tracking filter estimate and the second percentile tracking filter estimate extends a power source life of the power source based on a power consumption associated with a computational process relating to the first percentile tracking filter estimate and the second percentile tracking filter estimate.

2. The medical device of claim 1, wherein the method further comprising:
   (i) receiving a percentile value from a programmer.

3. The medical device of claim 1, wherein determining the first percentile tracking filter estimate and the second percentile tracking filter estimate each comprise determining a time-weighted function of the heart signal feature, and estimating one or more of the percentile tracking filter estimates from the time-weighted function.

4. The medical device of claim 3, wherein the time-weighted function is determined by first determining at least one parameter upon which the time-weighted function depends and where the time-weighted function is at least one of: a Gaussian distribution function; a Chi-square distribution function; an Uniform distribution function; and a Triangle distribution function.

5. The medical device of claim 1, wherein the first non-negative value and the second non-negative value are equal.

6. The medical device of claim 1, wherein the heart signal feature is the heart signal.

* * * * *